United States Patent
Fowlie

(10) Patent No.: US 11,612,916 B2
(45) Date of Patent: Mar. 28, 2023

(54) METHOD AND COMPOSITION FOR PULSE DOSE CLEANING OF PROCESS STREAMS

(71) Applicant: Phibro Animal Health Corporation, Teaneck, NJ (US)

(72) Inventor: David Fowlie, Concord, NC (US)

(73) Assignee: Phibro Animal Health Corporation, Teaneck, NJ (US)

( * ) Notice: Subject to any disclaimer, the term of this patent is extended or adjusted under 35 U.S.C. 154(b) by 65 days.

(21) Appl. No.: 17/158,900

(22) Filed: Jan. 26, 2021

(65) Prior Publication Data
US 2021/0229139 A1    Jul. 29, 2021

Related U.S. Application Data

(60) Provisional application No. 62/966,338, filed on Jan. 27, 2020.

(51) Int. Cl.
*B08B 9/032* (2006.01)
*B01D 1/30* (2006.01)
(Continued)

(52) U.S. Cl.
CPC ............. *B08B 9/0326* (2013.01); *B01D 1/30* (2013.01); *B01D 29/66* (2013.01); *B08B 3/08* (2013.01)

(58) Field of Classification Search
CPC ........... B08B 9/0326; B08B 3/08; B01D 1/30; B01D 29/66
See application file for complete search history.

(56) References Cited

U.S. PATENT DOCUMENTS

| 8,841,101 B2 | 9/2014 | Medoff |
| 2008/0311637 A1 | 12/2008 | Navapanich et al. |

(Continued)

FOREIGN PATENT DOCUMENTS

| AU | 2015340594 B2 | 5/2016 |
| CN | 1970713 A | 5/2007 |
| RU | 2705977 C1 * | 11/2019 |

OTHER PUBLICATIONS

Hatlar Group: "Clean-in-Place Best Practice Guidelines—Compare CIP with Best Practice for Smart Water Fund," Parts I-III, Aug. 1, 2010, retrieved from the Internet on Apr. 30, 2021, 113 pages.
(Continued)

*Primary Examiner* — Sharidan Carrillo
(74) *Attorney, Agent, or Firm* — Klarquist Sparkman, LLP

(57) ABSTRACT

Pulse dosing is used to administer a cleaning formulation into a fluid process stream flowing through structural components of a processing facility. The fluid process stream may contain corn, corn-derived products, or a combination thereof, or the fluid process stream may contain a process condensate, a rinse fluid, a cleaning fluid or any combination thereof. The processing facility may be an ethanol processing plant, a protein processing plant, a corn oil processing plant, an ethanol and corn oil processing plant, an ethanol and protein processing plant, or an ethanol, corn oil and protein processing plant. Pulse dosing may include administering the cleaning formulation into the fluid process stream for a period of x seconds every y minutes, with no administration of the cleaning formulation between the periods of x seconds.

18 Claims, 16 Drawing Sheets

(51) Int. Cl.
    *B01D 29/66*    (2006.01)
    *B08B 3/08*     (2006.01)

(56) References Cited

U.S. PATENT DOCUMENTS

| | | |
|---|---|---|
| 2010/0236581 A1 | 9/2010 | Fernholz et al. |
| 2010/0260918 A1 | 10/2010 | Wang et al. |
| 2014/0024064 A1 | 1/2014 | Burlew et al. |
| 2014/0106419 A1 | 4/2014 | Bazzana et al. |
| 2015/0087039 A1 | 3/2015 | Tandy |
| 2015/0176034 A1 | 6/2015 | Ramos et al. |
| 2015/0267225 A1 | 9/2015 | Bazzana et al. |
| 2015/0284659 A1 | 10/2015 | Young |
| 2017/0015938 A1 | 1/2017 | Xiao et al. |
| 2017/0028449 A1 | 2/2017 | Femholz et al. |
| 2019/0159479 A1 | 5/2019 | Yandell et al. |
| 2021/0229139 A1* | 7/2021 | Fowlie ................. B08B 9/0326 |

OTHER PUBLICATIONS

International Search Report and Written Opinion, dated May 12, 2021, issued in corresponding International Application No. PCT/US2021/015111, 14 pages.

* cited by examiner

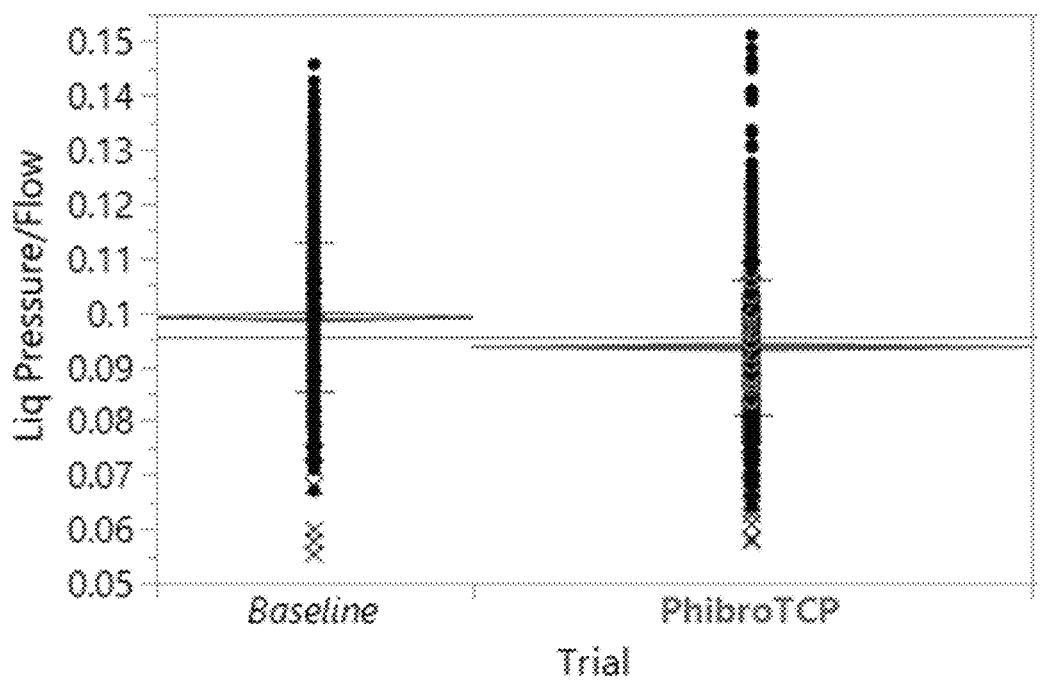
FIG. 6
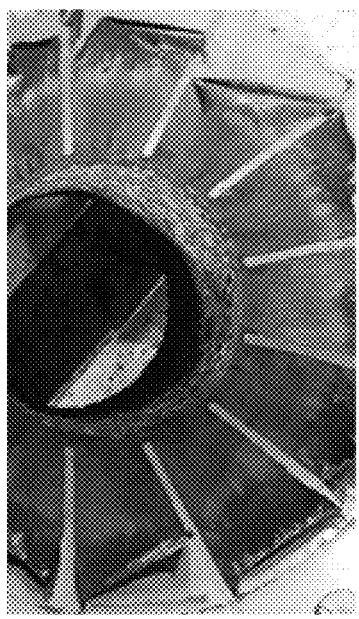   
FIG. 7   FIG. 8

METHOD AND COMPOSITION FOR PULSE DOSE CLEANING OF PROCESS STREAMS

CROSS-REFERENCE TO RELATED APPLICATION

This application claims the benefit of the earlier filing date of U.S. Provisional Application No. 62/966,338, filed Jan. 27, 2020, which is incorporated by reference in its entirety herein.

FIELD

This disclosure concerns a method for using pulse dosing to administer a cleaning formulation into a fluid process stream flowing through structural components of a processing facility.

BACKGROUND

Ethanol, protein, dry distillers grain, and/or oil processing plants typically use a cleaning in place (CIP) approach to controlling deposit buildups and bacteria that negatively impact ethanol, corn oil, and protein production. CIP events require plants to shut down sections of the plant periodically while it is still running to clean. These events require significant labor input and use of cleaning chemicals. CIP events also typically reduce plant efficiency while the cleaning cycle is ongoing since the section of the plant being cleaned is either partially or completely inoperable during the cleaning event. Methods for enhancing cleaning and yields of processing streams are needed in the art.

SUMMARY

Embodiments of a method for using pulse dosing to administer a cleaning formulation into a fluid process stream flowing through structural components of a processing facility are disclosed. Embodiments of cleaning formulations also are disclosed.

Embodiments of the disclosed method include using pulse dosing to administer a cleaning formulation into a fluid process stream flowing through structural components of a processing facility, the fluid process stream comprising (i) corn, corn-derived products, or a combination thereof, or (ii) a process condensate, a rinse fluid, a cleaning fluid, or any combination thereof. In some embodiments, pulse dosing comprises administering the cleaning formulation into the fluid process stream for a period of x seconds every y minutes, with no administration of the cleaning formulation between the periods of x seconds, wherein x and y independently are from 1 to 500. In any of the foregoing or following embodiments, an amount of the cleaning formulation administered into the fluid process stream may provide a concentration of 10 ppm to 50,000 ppm of the cleaning formulation in the fluid process stream during the period of x seconds. In any of the foregoing or following embodiments, In any of the foregoing or following embodiments, the processing facility may be an ethanol processing plant, a protein processing plant, a corn oil processing plant, an ethanol and corn oil processing plant, an ethanol and protein processing plant, or an ethanol, corn oil and protein processing plant. In some embodiments, the processing facility comprises one or more structural components selected from a heating and liquefaction unit, a heat exchanger unit, a propagation unit, a fermentation unit, a distillation unit, an evaporation unit, a centrifuge unit, a fiber separation unit, a protein separation unit, an oil separation unit, or any combination thereof. In some embodiments, the cleaning formulation is administered into the fluid process stream at, or upstream of, at least one of the one or more structural components.

In any of the foregoing or following embodiments, pulse dosing may be performed at each of two or more of the structural components of the processing facility for a period of x seconds every y minutes, with no administration of the cleaning formulation between the periods of x seconds at each of the two or more structural components, wherein each x and y independently is from 1 to 500. In some embodiments, an amount of the cleaning formulation administered into the fluid process stream at each of the two or more structural components independently provides a concentration of 10 ppm to 50,000 ppm of the cleaning formulation in the fluid process stream.

In some embodiments, the fluid process stream comprises corn, corn-derived products, or a combination thereof, and (i) the cleaning formulation is administered into, or upstream of, the heating and liquefaction unit, and a mean pressure increase over time within the heating and liquefaction unit is smaller than a mean pressure increase over time when the cleaning formulation is not administered using pulse dosing; or (ii) the cleaning formulation is administered into, or upstream of, the heat exchange unit, and a mean pressure increase over time within the heat exchange unit is smaller than a mean pressure increase over time when the cleaning formulation is not administered using pulse dosing; or (iii) the cleaning formulation is administered into, or upstream of, the heating and liquefaction unit, and a mean temperature drop over time within the heating and liquefaction unit is smaller than a mean temperature drop over time when the cleaning formulation is not administered using pulse dosing; or (iv) the cleaning formulation is administered into, or upstream of, the heat exchanger unit, and a mean temperature drop over time within the heat exchanger unit is smaller than a mean temperature drop over time when the cleaning formulation is not administered using pulse dosing; or (v) the cleaning formulation is administered into, or upstream of, the fiber separation unit, and a mean flow rate over a period of time through the fiber separation unit is greater than a mean flow rate over the period of time through the fiber separation unit when the cleaning formulation is not administered using pulse dosing; or (vi) the cleaning formulation is administered into, or upstream of, the protein separation unit, and a mean flow rate over a period of time through the protein separation unit is greater than a mean flow rate over the period of time through the protein separation unit when the cleaning formulation is not administered using pulse dosing; or (vii) the cleaning formulation is administered into, or upstream of, the oil separation unit, and a mean flow rate and/or oil production over a period of time through the oil separation unit is greater than a mean flow/or oil production over the period of time through the oil separation unit when the cleaning formulation is not administered using pulse dosing; or (viii) any combination of (i)-(vii).

In some embodiments, the fluid process stream comprises a process condensate, rinse fluid, or combination thereof, and the method further includes ceasing flow of a product process stream comprising corn-derived products through at least one of one or more structural components; initiating flow of the fluid process stream comprising the process condensate, rinse fluid, or combination thereof through the at least one of the one or more structural components; and using pulse dosing to administer the cleaning formulation into the fluid process stream comprising the process condensate, rinse fluid, or combination thereof. In certain embodiments, (i) pulse dosing comprises administering the cleaning formulation into the fluid process stream comprising the process condensate, rinse fluid, or combination thereof for a period of x seconds every y minutes, with no administration of the cleaning formulation between the periods of x seconds, wherein x and y independently are from 1 to 500; or (ii) an amount of the cleaning formulation is administered into the fluid process stream comprising the process condensate, rinse fluid, or combination thereof to provide a concentration of 10 ppm to 50,000 ppm of the cleaning formulation in the fluid process stream during the period of x seconds; or (iii) both (i) and (ii).

BRIEF DESCRIPTION OF THE DRAWINGS

FIG. 6 is a graph showing effects of pulse dose administration of a cleaning formulation to a mash bank on the ratio of pressure to flow rate over time as the fluid process stream flowed from the mash bank to the fermentation unit.

FIG. 7 is a photographic image of an oil separator unit disc following pulse dosing with a cleaning formulation administered to the fluid process stream.

FIG. 8 is a photographic image of oil separator unit discs following pulse dosing with a cleaning formulation administered to the fluid process stream and rinsing with a standard pressure washer.

DETAILED DESCRIPTION

Figure 1:
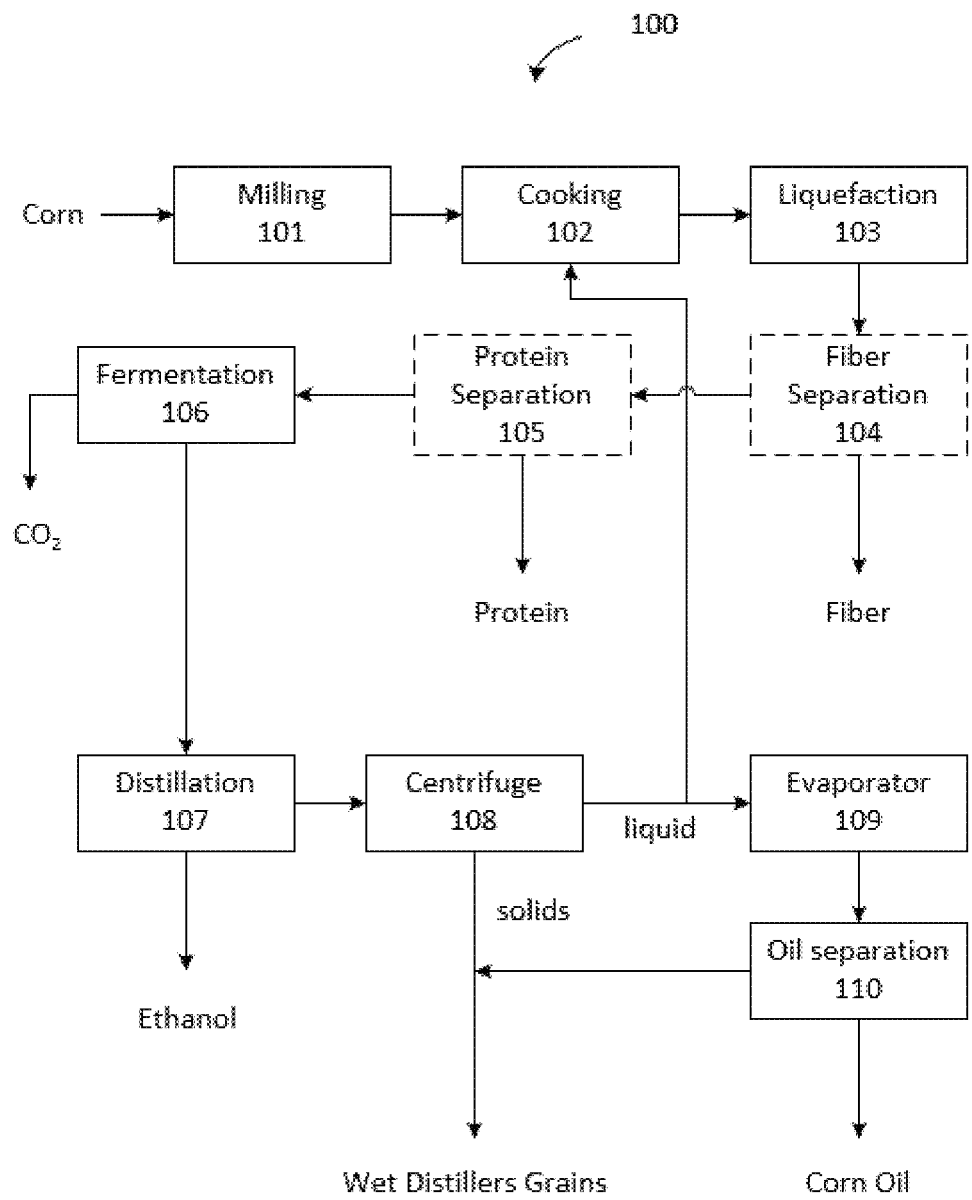
FIG. 1 is a block diagram of certain components and/or steps involved in an exemplary ethanol and oil processing plant.

Embodiments of a method for using pulse dosing to administer a cleaning formulation into a fluid process stream flowing through structural components of a processing facility are disclosed. In some embodiments, the fluid process stream comprises corn, corn-derived products, or a combination thereof. The fluid process stream may include, but is not limited to, mash, whole stillage and thin stillage. In some embodiments, the fluid process stream comprises a process condensate, a rinse fluid, a cleaning fluid, or any combination thereof. The process condensate may be, for example, condensate from an evaporation unit. Exemplary processing facilities include ethanol, protein, dry distillers grain, and/or corn oil processing plants. In some embodiments, the processing facility is an ethanol processing plant, a protein processing plant, a corn oil processing plant, an ethanol and corn oil processing plant, an ethanol and protein processing plant, or an ethanol, corn oil and protein processing plant.

I. EXPLANATION OF TERMS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Detergent: A substance that reduces the surface tension of water. Specifically, a surface-active agent, or surfactant, that concentrates at oil-water interfaces and exerts an emulsifying action. Detergents are classified as anionic, cationic, or nonionic, depending on their mode of chemical action. Nonionic detergents function via a hydrogen-bonding mechanism.

Downstream: As used herein, the term "downstream" refers to a point anywhere in the fluid process stream after a site (e.g., after a structural component) where a cleaning formulation is administered. Immediately downstream means a downstream point in the fluid process stream that is proximate the administration site.

Pulse dosing: Intermittent dosing, i.e., periods of dosing alternating with periods of no dosing.

Scale: A hard mineral coating or corrosion deposit composted of solids and sediments that collect on components in a processing facility as a process stream flows through or over the components.

Surfactant: A compound that reduces surface tension when dissolved in water or water solutions, or that reduces interfacial tension between two liquids. A surfactant molecule typically has a polar or ionic "head" and a nonpolar hydrocarbon "tail." Upon dissolution in water, the surfactant molecules aggregate and form micelles, in which the nonpolar tails are oriented inward and the polar or ionic heads are oriented outward toward the aqueous environment. Micelles typically are spherical in shape and small, with diameters of less than about 10 nm. The nonpolar tails create a nonpolar "pocket" within the micelle.

Upstream: When referring to the flow of a fluid process stream into a structural component, the term "upstream" refers to a point anywhere in the fluid process stream prior to entering the structural component. For example, upstream of an evaporator refers to any point in the fluid process stream before the fluid process stream flows through the evaporator. Immediately upstream means a point in the fluid process stream proximate entry into the structural component. With reference again to an evaporator, immediately upstream refers to a point in the fluid process stream just before it enters the evaporator and after it has flowed through all structural components located prior to the evaporator in the process.

II. INTRODUCTION

Continuous dosing of cleaning formulations into a process stream is a method used in processing plants of various industries to reduce fouling and/or bacterial contamination, thereby reducing frequency of facility shut-downs for cleaning. However, effective dosing levels for these types of formulations may not be practical or economical on a continuous dose basis. As disclosed herein, pulse dosing effectively controls deposit and bacteria formation in the plant while achieving these outcomes at an economically feasible cost and with reduced consumption of the cleaning formulations. At least some advantages of this approach to ethanol plants and other industries include, but are not limited to, (i) more efficient production of ethanol, oil, and protein; (ii) longer times between cleaning cycles, and/or (iii) less challenging cleaning events, providing significant maintenance savings in labor and cleaning chemicals.

In some of the disclosed implementations, the processing plant is an ethanol processing plant, a protein processing plant, an oil processing plant, an ethanol and oil processing plant, an ethanol and protein processing plant, or an ethanol, oil and protein processing plant. The oil may be corn oil. The process stream may be a fluid process stream comprising (i) corn, corn-derived products, or a combination thereof, or (ii) a process condensate, a rinse fluid, a cleaning fluid, or any combination thereof. In some embodiments, the fluid process stream includes, but is not limited to, mash, whole stillage and thin stillage. In some implementations, the process stream comprises a process condensate.

In some embodiments, a processing facility comprises one or more structural components selected from a milling unit, a heating/cooking and liquefaction unit, a heat exchanger unit (also referred to as a mash bank), a propagation unit (e.g., for propagating yeast), a fermentation unit, a distillation unit, an evaporation unit, a centrifuge unit, a fiber separation unit, a protein separation unit, an oil separation unit, or any combination thereof. Each unit may comprise one or more components arranged in series or in parallel. For instance, a distillation unit may comprise one, two, three, or more distillation columns. An evaporation unit may comprise, one, two, three, or more evaporators. A fiber separation unit may comprise a plurality of separation screens; for instance, the fiber separation unit may sequentially comprise primary, secondary, and tertiary separation screens.

A block diagram of one exemplary corn-to-ethanol processing facility 100 is shown in FIG. 1, which shows certain structural components and/or steps involved in corn-to-ethanol processing. Although the diagram of FIG. 1 shows one exemplary arrangement of the facility components, a person of ordinary skill in the art will understand that other arrangements are also possible and the exemplary arrangement of FIG. 1 is not necessarily preferred. The processing facility 100 includes a milling unit 101 where corn is milled to form a corn mash or fluid process stream. The milled corn process stream flows through a cooking unit 102 and a liquefaction unit 103, in which the corn mash is cooked and degraded into its component parts, e.g., fiber, protein, oils, etc. In some processing facilities, the process stream then flows through a fiber separation unit 104 and a protein separation unit, which remove fiber and protein, respectively, from the fluid process stream. In other processing facilities, the process stream flows directly from the liquefaction unit 103 to the fermentation unit 106. Although the exemplary arrangement of FIG. 1 shows fiber separation prior to protein separation, the person of ordinary skill in the art understands, particularly with the benefit of the present disclosure, that protein separation can be performed prior to fiber separation if desired or either process can be performed on its own. The fluid process stream then flows into the fermentation unit 106 where the fluid process stream is fermented to produce ethanol. The fermented fluid process stream flows into the distillation unit 107, which may comprise one or more distillation columns. Ethanol is distilled from the process stream, and the remainder of the process stream flows into the centrifuge 108, wherein solids are separated from the fluid process stream. The fluid process stream is then split, with part of the stream being recycled back to cooking unit 102 and part of the stream flowing to an evaporator unit 109, wherein low molecular-weight components, e.g. water and other volatile components, are removed from the fluid process stream, providing a fluid stream comprising a syrup. The syrup then flows into the oil separation unit 110, which separates corn oil from any remaining solids that formed in the evaporator unit 109. Although not shown explicitly, the person of ordinary skill in the art understands, particularly with the benefit of the present disclosure, that the cooking unit 102, liquefaction unit 103, fermentation unit 106, distillation unit 107, and/or evaporator unit 109 may comprise one or more heat exchangers.

III. PULSE DOSING METHOD

Disclosed herein are embodiments of a pulse dosing method for administering cleaning formulations into process streams, including corn-to-ethanol process streams as discussed herein. Formulation embodiments that can be used in such methods are described herein.

The disclosed method uses pulse dosing to administer a cleaning formulation into a fluid process stream flowing through structural components of a processing facility. In some embodiments, the fluid process stream comprises (i) corn, corn-derived products, or a combination thereof, or (ii) a process condensate, a rinse fluid, a cleaning fluid, or any combination thereof. In any of the foregoing or following embodiments, the cleaning formulation may comprise a detergent, an organic deposit control formulation, a scale inhibitor, a pH modifier, an oxidizer, a caustic solution or any combination thereof.

In any of the foregoing or following embodiments, pulse dosing may comprise administering the cleaning formulation into the fluid process stream for a period of x seconds every y minutes, with no administration of the cleaning formulation between the periods of x seconds. In some embodiments, x and y independently are from 1 to 500, such as 1-250, 1-150, 5-150, 5-100, 10-100, 10-90, 15-90, or 15-60. In certain examples, x and y independently are 5, 10, 15, 30, 45, 60, or 90. In some non-limiting examples, the cleaning formulation is pulse dosed into the fluid process stream for a period of 5 seconds every 5 minutes, 10 seconds every 10 minutes, 15 seconds every 15 minutes, 30 seconds every 30 minutes, 45 seconds every 45 minutes, 60 seconds every 60 minutes, or 90 seconds every 90 minutes. In any of the foregoing or following embodiments, x and y may be the same or different. In some embodiments, x and y are the same, e.g., 30 seconds every 30 minutes. In some embodiments, x and y are different, e.g., 15 seconds every 30 minutes or 45 seconds every 30 minutes.

Administering the cleaning formulation into the process stream via pulse dosing may be performed by any suitable method. In some embodiments, administering is performed by flowing, injecting, or spraying the cleaning formulation into the fluid process stream. Administration may be performed at a continuous or substantially continuous rate throughout each period of x seconds. The amount of cleaning formulation administered is selected to provide a desired concentration in the fluid process stream. In some embodiments, the cleaning formulation is a fluid and a volume sufficient to provide a desired concentration is administered into the fluid process stream over each period of x seconds.

In any of the foregoing or following embodiments, the cleaning formulation may be pulse dosed into the fluid process stream to provide any desired or effective concentration of the cleaning formulation in the fluid process stream during the period of x seconds. In some embodiments, the cleaning formulation is pulse dosed into the fluid process stream to provide a concentration of 10 ppm to 50,000 ppm of the cleaning formulation in the fluid process stream during the period of x seconds. The concentration may be determined at or immediately downstream of the site where the cleaning formulation is administered. In some embodiments, the concentration is 10 ppm to 25,000 ppm, 15 ppm to 20,000 ppm 20 ppm to 15,000 ppm, 50 ppm to 10,000 ppm, 100 ppm to 5,000 ppm, 100 ppm to 2,000 ppm, 125 ppm to 2000 ppm, 250 ppm to 2000 ppm, 250 ppm to 1500 ppm, 250 ppm to 1000 ppm, or 250 ppm to 750 ppm. The processing facility may be an ethanol processing plant, a protein processing plant, a corn oil processing plant, an ethanol and corn oil processing plant, an ethanol and protein processing plant, or an ethanol, corn oil and protein processing plant. In some embodiments, the processing facility comprises one or more structural components selected from a heating and liquefaction unit, a heat exchanger unit, a propagation unit, a fermentation unit, a distillation unit, an evaporation unit, a centrifuge unit, a fiber separation unit, a protein separation unit, an oil separation unit, or any combination thereof, as previously described. The cleaning formulation may be administered into the fluid process stream in, or upstream of, at least one of the one or more units using pulse dosing. In some embodiments, the cleaning formulation is administered into the fluid process stream in, or upstream of, the heating and liquefaction unit, the heat exchanger unit, the evaporation unit, the fiber separation unit, the protein separation unit, the oil separation unit, or any combination thereof.

In any of the foregoing or following embodiments, pulse dosing may be performed at different stages of the process. For example, a cleaning formulation may be administered via pulse dosing into the fluid process stream in, or upstream of, two or more of the processing facility structural components. The cleaning formulations administered into the fluid process stream at each of the two or more structural components may have the same chemical composition or cleaning formulations with different chemical compositions may be administered at each of the two or more structural components. For instance, an organic deposit control formulation may be administered into the fluid process stream at a first structural component, and a scale inhibitor formulation may be administered into the fluid process stream at a subsequent structural component. In any of the foregoing or following embodiments, the pulse dosing may be performed at each of the two or more structural components for a period of x seconds every y minutes, with no administration of the cleaning formulation between the periods of x seconds at each of the two or more structural components, wherein each x and y independently is from 1 to 500, such as 1-250, 1-150, 5-150, 5-100, 10-100, 10-90, 15-90, or 15-60. In certain examples, x and y independently are 15, 30, 45, 60, or 90. In some embodiments, x=y at each one of the two or more structural components, e.g., 60 seconds every 60 minutes. In other embodiments, x≠y, e.g., 20 seconds every 30 minutes. In some embodiments, x and y are the same at a given structural component, but may differ from structural component to structural component within the processing facility. For instance, pulse dosing may be performed for 30 seconds every 30 minutes at a first structural component, and for 60 seconds every 60 minutes at a subsequent structural component. In some implementations, x and y are the same at each of the two or more structural component. For example, pulse dosing may be performed for 30 seconds every 30 minutes at each of the two or more structural components. Additionally, an amount of cleaning formulation administered via pulse dosing to each of the two or more structural components independently provides a concentration of 10 ppm to 50,000 ppm of the cleaning formulation in the fluid process stream. In some embodiments, the concentration at each of the two or more structural components independently is 10 ppm to 25,000 ppm, 15 ppm to 20,000 ppm, 20 ppm to 15,000 ppm, 50 ppm to 10,000 ppm, 100 ppm to 5,000 ppm, 100 ppm to 2,000 ppm, 125 ppm to 2000 ppm, 250 ppm to 2000 ppm, 250 ppm to 1500 ppm, 250 ppm to 1000 ppm, or 250 ppm to 750 ppm. For instance, in one non-limiting example, the cleaning formulation may be administered to the heat exchanger unit for 30 seconds every 30 minutes to provide a concentration of 250 ppm in the fluid process stream at or immediately downstream of the heat exchanger unit, and also may be administered to the fiber separation unit for 30 seconds every 30 minutes to provide a concentration of 500 ppm in the fluid process stream at or immediately downstream of the fiber separation unit.

In another example, the fiber separation unit may comprise one or more separation screens, and the cleaning formulation is administered into the fluid process stream via pulse dosing upstream of at least one of the one or more of the separation screens. In one embodiment, the fiber separation unit comprises a primary separation screen, a secondary separation screen, and a tertiary separation screen. In this embodiment, the cleaning formulation is administered into the fluid process stream via pulse dosing at the secondary separation screen to provide a first concentration of the cleaning formulation in the fluid process stream at or proximate the secondary separation screen, and the cleaning formulation is administered into the fluid process stream via pulse dosing at the tertiary separation screen to provide a second concentration of the cleaning formulation in the fluid process stream at or proximate the tertiary separation screen. In some implementations, the second concentration is less than the first concentration. For instance, the first concentration may be 500 ppm and the second concentration may be 250 ppm, or the first concentration may be 750 ppm, and the second concentration may be 500 ppm or 250 ppm. Additionally, each pulse dosing interval (x and y, as described herein) at each screen may be the same or different. In one implementation, the pulse dosing intervals at the secondary and tertiary screens are the same such that the cleaning formulation is dosed to into the fluid process stream at each of the secondary and tertiary screens for 30 seconds every 30 minutes.

In some embodiments, the fluid process stream comprises corn, corn-derived products, or a combination thereof, and pulse dosing the cleaning formulation into the fluid process stream at mash banks (heating and liquefaction units) and heat exchangers can improve heat transfer efficiency, which provides energy savings, as well as control of bacterial buildup in the mash banks that can impact fermentation further downstream, leading to less bacteria (and more ethanol) and extending time between CIP cleaning cycles. Metrics associated with such embodiments can include delta pressure, delta temperature, in beer, and mash flows. In some implementations, the cleaning formulation is administered via pulse dosing into, or upstream of, the heating and liquefaction unit, and a mean pressure increase and/or temperature drop over time within the heating and liquefaction unit is smaller than a mean pressure increase and/or temperature drop over time when the cleaning formulation is not administered using pulse dosing. In some implementations, the cleaning formulation is pulse dosed into, or upstream of, the heat exchange unit, and a mean pressure increase and/or temperature drop over time within the heat exchange unit is smaller than a mean drop pressure increase and/or temperature drop over time when the cleaning formulation is not administered using pulse dosing as described herein. For instance, the mean pressure increase and/or temperature drop over time may be smaller than a mean drop in pressure and/or temperature when (i) no cleaning formulation is administered, and/or (ii) an equivalent low dose of the cleaning formulation is continuously administered, i.e., an amount of the cleaning formulation is continuously added to the fluid process stream to provide a constant or substantially constant concentration (e.g., a concentration varying by no more than ±10% relative to an average concentration). Continuous administration may be performed at a single point within the processing facility, e.g., into or upstream of the heating or liquefaction unit, or upstream of the fiber separation unit. An equivalent low dose is determined by calculating the dose that would be provided if the pulse dose is instead continuously administered; that is, pulse dosing to provide a cleaning formulation concentration of 500 ppm in the fluid process stream for 60 seconds every 60 minutes is equivalent to continuously administering to provide a constant or substantially constant cleaning formulation concentration of 8.3 ppm in the fluid process stream. In certain examples, the mean pressure increase over time at a given structural component of the processing facility is at least 1% smaller, at least 2% smaller, at least 5% smaller or at least 10% smaller than the mean pressure increase when the cleaning formulation is not administered using pulse dosing. Pressure increases as deposits build up on the structural component(s) and restrict flow of the fluid process stream. Pulse dosing effectively reduces the rate of deposit formation and thus reduces the rate at which pressure increases at the structural component. The mean pressure increase over time under a pulse dosing regimen may be 1-20%, 2-20%, 5-20%, or 10-15% smaller than the mean pressure increase over time in the absence of pulse dosing. In some examples, the mean temperature drop over time is at least 1% smaller, at least 2% smaller, at least 5% smaller, at least 10% smaller than the mean temperature drop over time when the cleaning formulation is not administered using pulse dosing. As deposits build up on structural components, the temperature drops over time. Temperature drops may be attributed to reduced flow rate and/or restricted heat transfer due to the deposits. The mean temperature drop under a pulse dosing regimen may be 1-15%, 2-15%, 5-15%, or 10-15% smaller than the mean temperature drop in the absence of pulse dosing.

In some embodiments, cleaning formulation that is pulse dosed into a fluid process stream comprising corn, corn-derived products, or a combination thereof, at mash banks will flow subsequently into a propagator, removing deposits and bacteria that negatively impact ethanol production, and extending time between CIP cleaning cycles. In additional embodiments, cleaning formulation that is dosed into the fluid process stream at the mash banks will flow into the fermentation fill headers, removing deposits and bacteria that negatively impact ethanol production extending time between CIP cycles and improving ethanol production efficiency. Metrics associated with such embodiments can include lactic acid delta (change in lactic acid values over time) and acetic acid delta.

In yet some additional embodiments, cleaning formulation that is pulse dosed into the mash banks will flow into the fermentation, delivering corn mash that has lower bacteria populations that negatively impact ethanol production, thereby extending time between CIP cleaning cycles and providing improved ethanol production efficiency. Metrics associated with such embodiments can include lactic acid delta and acetic acid delta.

In some embodiments, pulse dosing the cleaning formulation into a fluid process stream comprising corn, corn-derived products, or a combination thereof at the evaporators to control deposit buildup can be used to improve heat transfer and evaporation efficiency and extending time between CIP cleaning cycles. Metrics associated with such embodiments can include steam use, efficiency, and $1^{st}$ and $2^{nd}$ effect pressures.

In yet some additional embodiments, cleaning formulation that is pulse dosed into the fluid process stream at the evaporators will flow downstream to the oil recovery system, removing deposits on oil separation equipment, thereby providing increased oil production and extending time between CIP cleaning cycles. Metrics associated with such embodiments can include flow rate through the oil separation unit and averaged oil production. In some implementations, the cleaning formulation is administered via pulse dosing into, or upstream of, the oil separation unit, and a mean flow rate over a period of time through the oil separation unit is greater than a mean flow rate over the period of time through the oil separation unit when the cleaning formulation is not administered using pulse dosing. For instance, the mean flow rate may be greater and/or may drop more slowly than a flow rate when (i) no cleaning formulation is administered, and/or (ii) an equivalent low dose of the cleaning formulation is continuously administered. The flow rate through the oil separation unit under a pulse dosing regimen may be at least 0.1% greater, at least 0.2% greater, or at least 0.3% greater than an average flow rate through the oil separation unit in the absence of pulse dosing. The flow rate under a pulse dosing regimen may be 0.1-10%, 0.1-5%, or 0.1-2% greater than the flow rate in the absence of pulse dosing. The increased flow rate may be attributed to a reduced amount of deposits forming on structural components of the processing facility, thereby producing less restricted flow through conduits, separation screens, and/or other structural components through which the process stream flows. A person of ordinary skill in the art understands that flow rate can also be increased by the plant independently of any impact of pulse dosing.

In some embodiments, using pulse dosing to administer the cleaning formulation into a fluid process stream comprising corn, corn-derived products, or a combination thereof, at, or immediately upstream of, separation screens that separate corn fiber from the protein and fermentable portions of corn can be used to improve separation efficiency and thereby extending time between CIP cleaning cycles. Or, using pulse dosing to administer the cleaning formulation into the fluid process stream at the protein separation clarifier can be used to improve protein production efficiency, thereby extending time between CIP cleaning cycles. Metrics associated with such embodiments can include the flow rate, time between cleanings, and/or protein production. In some implementations, the cleaning formulation is pulse dosed into the fluid process stream at, or upstream of, the fiber separation unit (or upstream of one or more of a plurality of separation screens of the separation unit), and a mean flow rate over a period of time through the fiber separation unit is greater than a mean flow rate over the period of time through the fiber separation unit when the cleaning formulation is not administered using pulse dosing. In some implementations, the cleaning formulation is pulse dosed into the fluid process stream at, or upstream of, the protein separation unit, and a mean flow rate over a period of time through the protein separation unit is greater than a mean flow rate over the period of time through the protein separation unit when the cleaning formulation is not administered using pulse dosing. For instance, the mean flow rate may be greater and/or may drop more slowly than a flow rate when (i) no cleaning formulation is administered, and/or (ii) an equivalent low dose of the cleaning formulation is continuously administered. The flow rate through the fiber separation unit and/or protein separation unit under a pulse dosing regimen may be at least 0.1% greater, at least 0.2% greater, or at least 0.3% greater than an average flow rate through the fiber separation unit and/or protein separation unit in the absence of pulse dosing. The flow rate under a pulse dosing regimen may be 0.1-10%, 0.1-5%, or 0.1-2% greater than the flow rate in the absence of pulse dosing.

In some embodiments, the fluid process stream comprises a process condensate, a rinse fluid, a cleaning fluid, or any combination thereof, and pulse dosing is used as part of a CIP process. The process condensate may be obtained, for example, from an evaporator unit of the processing facility. The process condensate may comprise water and other low molecular weight, volatile components. In some implementations, a rinse fluid comprises water or an aqueous buffered solution.

In some embodiments, a CIP process includes ceasing flow of a product process stream comprising corn-derived products through at least one of the one or more structural components of the processing facility, initiating flow of the fluid process stream comprising the process condensate, rinse fluid, or combination thereof through the at least one of the one or more structural components, and using pulse dosing to administer the cleaning formulation into the fluid process stream comprising the process condensate, rinse fluid, or combination thereof. In certain embodiments, pulse dosing comprises administering the cleaning formulation into the fluid process stream comprising the process condensate, rinse fluid, or combination thereof for a period of x seconds every y minutes, with no administration of the cleaning formulation between the periods of x seconds, wherein x and y independently are from 1 to 500. Frequently, the values of x and y in a CIP process in which the process stream comprises a process condensate and/or a rinse fluid are greater than the values of x and y used when the process stream is a product process stream comprising corn, corn-derived products, or a combination thereof. For instance, in some embodiments of a CIP process, the cleaning formulation is added for a period of 60-300 seconds every 350-900 minutes. In certain embodiments of the CIP process, $x \neq y$.

In any of the foregoing or following embodiments, an amount of the cleaning formulation may be administered into the fluid process stream comprising the process condensate, rinse fluid, or combination thereof to provide a concentration of 10 ppm to 50,000 ppm of the cleaning formulation in the fluid process stream during the period of x seconds. In any of the foregoing or following embodiments, the cleaning formulation may comprise a detergent, an organic deposit control formulation, a scale inhibitor, a pH modifier, an oxidizer, a caustic solution, or any combination thereof.

In some embodiments, a CIP process comprises a first stage and a second stage. Pulse dosing as described herein may be used in either stage of the CIP process. In some embodiments, the first stage can comprise adding a surfactant-based detergent cleaning formulation to a process stream wherein the cleaning formulation (e.g., an amount to provide a concentration of 500 ppm) is added to a process condensate pre-rinse for a period of several minutes, sequentially or substantially simultaneously with a solution of a cleaning formulation comprising nitric acid and a detergent (e.g., a 1.5% solution) for a period of several hours. The first stage may range from 1 hour to several hours depending on the amount and composition of the deposits to be removed, with longer times being used when a greater amount of deposited material is present and/or when the deposited material is more difficult to remove. In some implementations, the cleaning formulation is added to the process condensate pre-rinse for 4 minutes, sequentially or substantially simultaneously with a solution of a cleaning formulation comprising nitric acid and a detergent (e.g., a 1.5% solution) for 6 to 8 hours. In this example, pulse dosing is performed for 240 seconds (4 minutes) every 360-480 minutes (6-8 hours). Stage 2 can comprise adding a lower concentration of the surfactant-based detergent cleaning formulation (e.g., 250 ppm) to the process condensate pre-rinse for a period of time (e.g., 4 minutes), sequentially or substantially simultaneously with (i) an organic deposit control formulation; and/or (ii) a cleaning formulation comprising nitric acid and a detergent for a period of time (e.g., 6 to 8 hours). The second stage may range from 1 hour to several hours depending on the amount and composition of the deposits to be removed. In one example, the organic deposit control formulation is added in an amount to provide a concentration of 250 ppm for 1 minute per hour, comprising two 30-second dosages (e.g., 4.5 gallons/day or 135 gallons/month). In one example, the cleaning formulation comprising nitric acid and a detergent is a 1.0% solution. In some embodiments, such methods can be used for mash banks and heat exchangers and can be used every 12 to 15 hours.

In some embodiments, the first stage can comprise adding a surfactant-based detergent cleaning formulation to a process stream wherein, for example, the cleaning formulation is added to a process condensate pre-rinse for 5 minutes in an amount to provide a concentration of 500 ppm in the process condensate, sequentially or substantially simultaneously with a 1.5% solution of a cleaning formulation comprising nitric acid and a detergent for 1 hour (as a spray ball, in some embodiments). Stage 2 can comprise, for example, adding the surfactant-based detergent cleaning formulation to the process condensate pre-rinse for 5 minutes in an amount to provide a concentration of 250 ppm, sequentially or substantially simultaneously with a 1.0% solution of a cleaning formulation comprising nitric acid and a detergent for 1 hour (as a spray ball, in some embodiments). In some embodiments, such methods can be used for propagation and can be used every 12 to 15 hours.

In some embodiments, the first stage can comprise adding a surfactant-based detergent cleaning formulation to a process stream wherein, for example, the cleaning formulation is added to a process condensate pre-rinse for 5 minutes in an amount to provide a concentration of 500 ppm, sequentially or substantially simultaneously with a 1.5% solution of a cleaning formulation comprising nitric acid and a detergent for 1 hour (as a spray ball, in some embodiments) and a 45-minute cooling. Stage 2 can comprise, for example, adding the surfactant-based detergent cleaning formulation to the process condensate pre-rinse for 5 minutes in an amount to provide a concentration of 250 ppm, sequentially or substantially simultaneously with a 1.0% solution of a cleaning formulation comprising nitric acid and a detergent for 1 hour (as a spray ball, in some embodiments) and a 45-minute cooling. In some embodiments, such methods can be used for fermenters and can be used every 12 to 15 hours.

In some embodiments, the first stage can comprise adding a surfactant-based detergent cleaning formulation to a process stream wherein, for example, the cleaning formulation is added to a process condensate pre-rinse for 5 minutes in an amount to provide a concentration of 500 ppm, sequentially or substantially simultaneously with a 1.5% solution of a cleaning formulation comprising nitric acid and a detergent for 45 minutes. Stage 2 can comprise, for example, adding the surfactant-based detergent cleaning formulation to the process condensate pre-rinse for 5 minutes in an amount to provide a concentration of 250 ppm, sequentially or substantially simultaneously with a 1.0% solution of a cleaning formulation comprising nitric acid and a detergent for 45 minutes. In some embodiments, such methods can be used for fermenter fill headers and can be used every 48 hours per fermentation cycle.

In some embodiments, the first stage can comprise adding a surfactant-based detergent cleaning formulation to a process stream wherein, for example, the cleaning formulation is added to a process condensate pre-rinse for 45 minutes in an amount to provide a concentration of 1000 ppm, sequentially or substantially simultaneously with (i) a 1.5% solution of a cleaning formulation comprising nitric acid and a detergent for 4 hours; and/or (ii) a scale inhibitor formulation, which can be added in an amount to provide a concentration of 20-30 ppm. Stage 2 can comprise, for example, adding the surfactant-based detergent cleaning formulation to the process condensate pre-rinse for 45 minutes in an amount to provide a concentration of 500 ppm, sequentially or substantially simultaneously with (i) a 1.0% solution of a cleaning formulation comprising nitric acid and a detergent for 4 hours; (ii) an organic deposit control formulation added for 1 minute per hour in an amount to provide a concentration of 500 ppm, comprising two 30-second doses (e.g., 7.2 gallons per day or 216 gallons per month); and/or (iii) a scale inhibitor formulation, which can be added in an amount to provide a concentration of 20-40 ppm. In some embodiments, such methods can be used for evaporators and can be used once per week.

In some embodiments, the first stage can comprise adding a surfactant-based detergent cleaning formulation to a process stream wherein, for example, the cleaning formulation is added to a process condensate pre-rinse in an amount to provide a concentration of 1500 ppm. Stage 2 can comprise adding 1000 ppm of the surfactant-based detergent cleaning formulation to the process condensate pre-rinse. In some embodiments, such methods can be used for oil separation and can be used every 7-10 days.

Embodiments of the disclosed pulse dosing method provide advantages not realized by continuous dosing methods with an equivalent concentration of the cleaning formulation and/or methods in which no cleaning formulation is administered into the fluid process stream. As discussed herein, pulse dosing the cleaning formulation into a process stream comprising corn, corn-derived products, or a combination thereof may provide smaller pressure increases and/or temperature drops through a mash bank (heating and liquefaction unit) or heat exchanger compared to continuous dosing with an equivalent lower concentration of the cleaning formulation and/or methods relying solely on cleaning-in-process (CIP) at periodic intervals. And, as described herein, some embodiments of the pulse dosing method increase flow rates or provide smaller flow rate decreases through separation screens of a fiber separation unit and/or protein separation unit compared to continuous dosing into the process stream comprising corn, corn-derived products, or a combination thereof with an equivalent lower concentration of the cleaning formulation and/or methods relying on periodic CIP only. Embodiments of the disclosed pulse dosing method advantageously provide lower levels of product contamination (e.g., ethanol and/or oil contamination with cleaning formulation components) compared to methods utilizing continuous dosing into the process stream comprising corn, corn-derived products, or a combination thereof at effective levels, e.g., continuous dosing of the cleaning formulation to provide concentrations of 100 ppm or more. Additionally, the pulse dosing method may extend cleaning-in-process intervals requiring plant shutdowns for cleaning compared to continuous dosing or no-dosing methods of operating the processing plant. For instance, CIP intervals may be increased 25%, 50%, 75%, or even 100% or more when pulse dosing is used. In one example, cleaning intervals were increased from every 4-5 hours to every 8 hours when a cleaning formulation was administered using pulse dosing to screens of a fiber separation unit. Cleaning during CIP events following pulse dosing may be easier, requiring less effort, less intensive methods, and/or less time than cleaning during CIP events following continuous dosing with an equivalent lower concentration of the cleaning formulation and/or methods relying on periodic CIP only. Pulse dosing during CIP events advantageously may shorten the CIP event and/or reduce an amount of cleaning formulation required for effective cleaning compared to a CIP process utilizing continuous dosing of the cleaning formulation.

IV. FORMULATIONS

Formulations that can be used in embodiments of the pulse dosing method disclosed herein can include surfactant-based detergent cleaning formulations (e.g., PHIBROCLEAN™) cleaning formulations comprising nitric acid and a detergent (e.g., PHIBRO ACT™), scale inhibitor formulations (e.g., PHIBRO SI™), organic deposit control formulations (e.g., PHIBRO DC™), pH modifiers (e.g., acid, alkali, or a buffer), an oxidizer, a caustic solution, or any combination thereof. In some embodiments, the formulation is a nitric acid-containing formulation. In such embodiments, the nitric acid provides high strength dissolution power and the built-in detergent provides improved penetration of the cleaning solution into deposits and removal of organic scale components. Such formulations also are GRAS-compatible. And, such formulation embodiments are effective in dissolving and removing beer stone (e.g., calcium and magnesium oxalate), calcium/magnesium phytate, struvite, combined organic/inorganic compounds, and combinations thereof. See, for example, FIG. 3 as compared to FIG. 2. Pulse dosing a nitric acid-containing formulation may reduce frequency and duration of CIP events and/or reduce CIP chemical usage.

In some embodiments, the formulation is a detergent cleaner. Using such formulations in pulse dosing methods can improve cleaning through detergent action, improve penetration of such solutions into deposits and assist in their removal, and provide potential savings in caustic usage by facilitating the use of lower caustic concentrations and improved caustic solution stability, extending intervals between cleaning shutdowns, and combinations thereof. Also, such formulations are Food Safety Modernization Act (FSMA) compliant. In some embodiments, such formulations can be added via pulse dosing to the fluid process stream remove organic material prior to a subsequent caustic CIP cycle, which can improve caustic solution stability and overall CIP effectiveness, reduce frequency and duration of CIP events, and/or reduce CIP chemical usage. See, for example, FIG. 4 (detergent and caustic) as compared to FIG. 5 (caustic only).

In yet additional embodiments, the formulation can be a scale inhibitor, which is effective in reducing formation of beer stone (e.g., calcium and magnesium oxalate), struvite, calcium and magnesium phytates, combined organic and inorganic deposits, and combinations thereof. In some embodiments, scale formation can be reduced by threshold inhibition, wherein pulse dosing modifies the chemistry of the fluid process stream to favor the formation of soluble compounds versus insoluble compounds; sequestration, wherein the physical and chemical interaction of potential scale forming components is controlled, reducing scale formation reactions; and/or crystal modification, which reduces the density of scale deposits that form, making them more amorphous and less crystalline in nature and/or makes fouling that does occur easier to remove during subsequent cleaning events.

In yet some additional embodiments, the formulation can comprise an organic deposit controlling formulation. Such embodiments can be pulse dosed directly into the process stream to control organic deposit buildup, can improve overall process consistency and performance, reduce frequency and duration of CIP events, and/or reduce CIP chemical usage.

Figure 2:
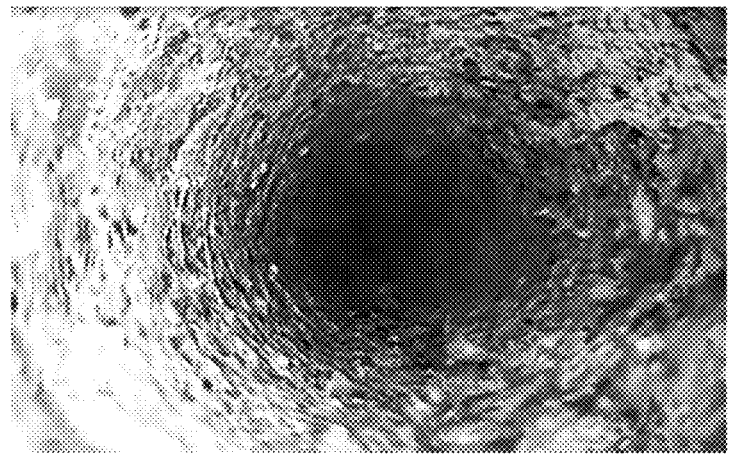
FIG. 2 is a photographic image of an evaporator tube prior to cleaning.
Figure 3:
FIG. 3 is a photographic image of the evaporator tube of FIG. 2 after cleaning with a cleaning formulation comprising nitric acid and a detergent using a standard CIP process.
Figure 4:
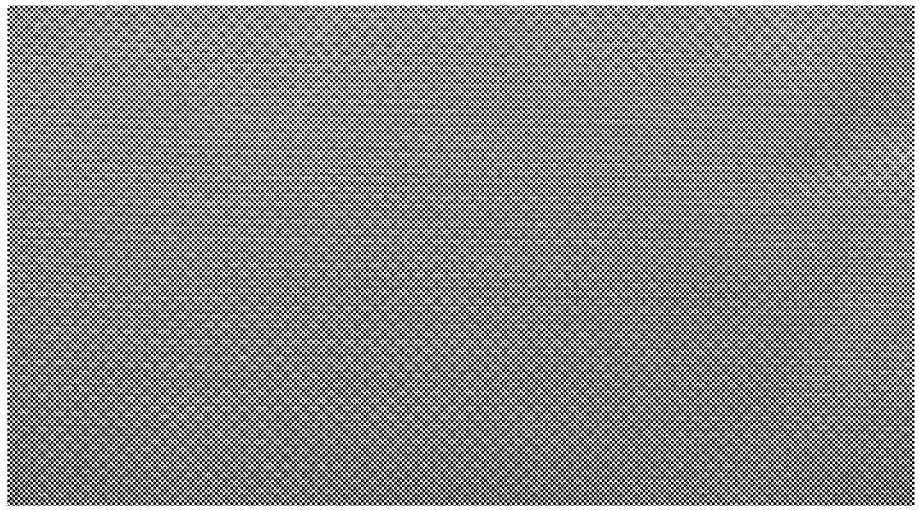
FIG. 4 is a photographic image of a screen cleaned with a surfactant-based formulation and a caustic.
Figure 5:
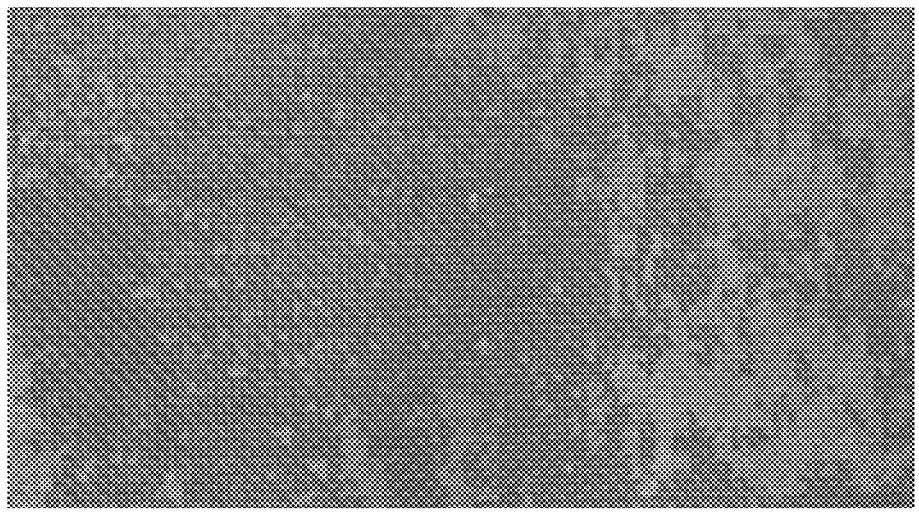
FIG. 5 is a photographic image of a screen cleaned with a caustic only using a standard CIP process.

Comparisons of various processing components (e.g., evaporator tubes) before and after treatment in a standard CIP process with a formulation of the present disclosure are shown in FIGS. 2 and 3 respectively. FIGS. 4 and 5 show a comparison between a screen cleaned in a standard CIP process with a formulation of the present disclosure (FIG. 4) as compared to using a caustic only (FIG. 5).

V. EXAMPLES

Example 1

PhibroDC™ cleaning formulation was administered into a fluid process stream (corn mash) of an ethanol- and oil-processing plant at several locations using pulse dosing.

The PhibroDC™ cleaning formulation was administered into the mash bank for 60 seconds every 60 minutes to provide a concentration of 250 ppm. FIG. 6 is a graph showing effects of the pulse dose administration on the ratio of pressure to flow rate over time as the fluid process stream flowed from the mash bank to the fermentation unit. As shown in FIG. 6, the pulsed dosing regimen reduced the pressure/flow ratio.

PhibroDC™ cleaning formulation was administered into the last evaporator before oil recovery for 60 seconds per 60 minutes to provide a concentration of 500 ppm. Typically, day-long hydroblasting is required to remove deposits and take apart the oil recovery stacked disc assembly for cleaning. However, following pulse dose administration of the cleaning formulation, deposited material on the discs began to peel off without hydroblasting (FIG. 7), and the assembly was easily separated and cleaned with a standard pressure washer (FIG. 8).

Figure 9:
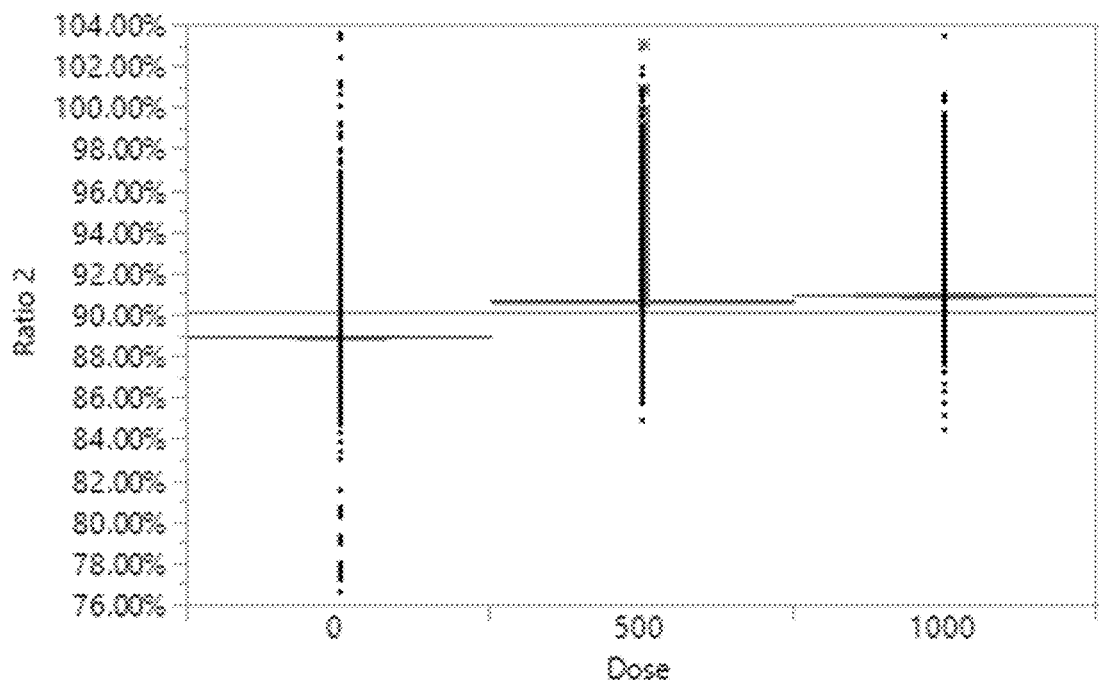
FIG. 9 is a graph showing effects of pulse dose administration of a cleaning formulation at doses of 0, 500, and 1000 ppm on flow rate through a secondary screen of a fiber separation unit.

The PhibroDC™ cleaning formulation was administered upstream of the secondary and/or tertiary screens of the fiber separation unit via pulse dosing. The dosing was 500 ppm or 1000 ppm for 30 seconds every 30 minutes. The effects on flow rate through the secondary screen without pulse dosing and at the two administered doses are shown in FIG. 9 and Table 1. The calculated ratios eliminate noise in the data. Results were analyzed using a one-way Anova test and student's t test. The differing connecting letters indicate that the results are statistically different. Notably, the graph shows that there is less data indicating a low flow rate when the pulse dosing is used. Pulse dose administration improved the flow rate consistency. The connecting letters report shows that the results are statistically different.

TABLE 1

| Dose (ppm) | Mean | Std. Error | Lower 95% | Upper 95% | Connecting letter |
|---|---|---|---|---|---|
| 0 | 0.890145 | 0.00025 | 0.88966 | 0.89063 | A |
| 500 | 0.907513 | 0.00019 | 0.90714 | 0.90789 | B |
| 1000 | 0.910233 | 0.00037 | 0.90951 | 0.91095 | C |

Figure 10:
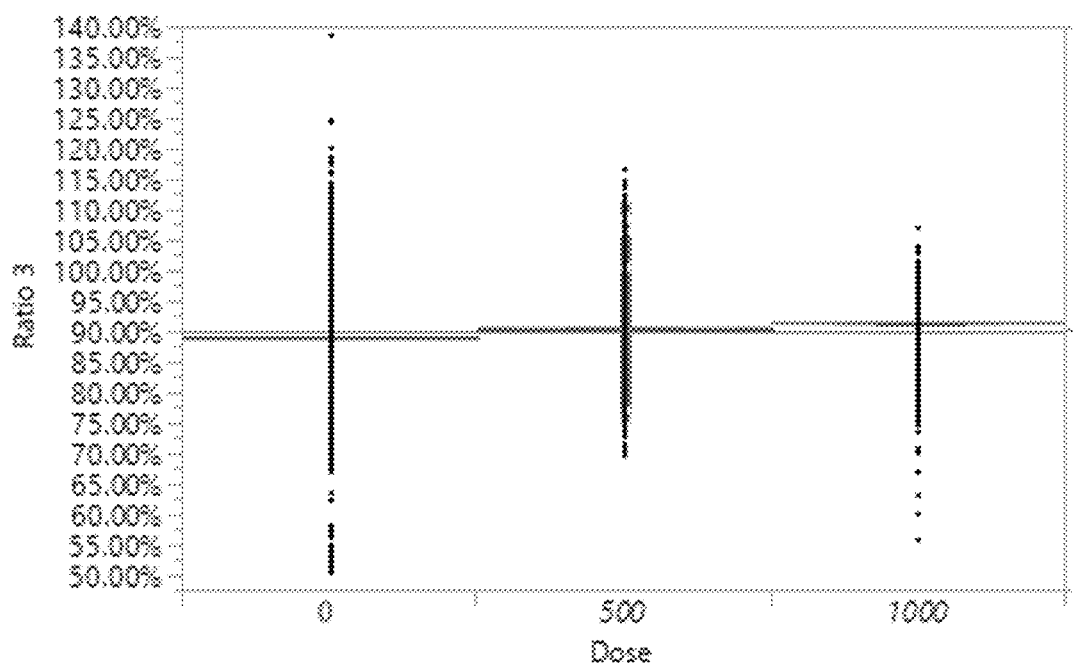
FIG. 10 is a graph showing effects of pulse dose administration of a cleaning formulation at doses of 0, 500, and 1000 ppm on flow rate through a secondary screen of a fiber separation unit.

The effects on flow rate through the tertiary screen without pulse dosing and at the two administered doses are shown in FIG. 10 and Table 2. Results were analyzed using a one-way Anova test and student's t test. Notably, the graph shows that there is less data indicating a low flow rate when the pulsed dosing is administered. The effects of pulsed dosing at the tertiary screen is less pronounced since the flow rate is affected also by flow through the primary and secondary screens.

TABLE 2

| Dose (ppm) | Mean | Std. Error | Lower 95% | Upper 95% |
|---|---|---|---|---|
| 0 | 0.892607 | 0.00070 | 0.89123 | 0.89398 |
| 500 | 0.907109 | 0.00055 | 0.90604 | 0.90818 |
| 1000 | 0.916347 | 0.00105 | 0.91432 | 0.91843 |

Figure 11:
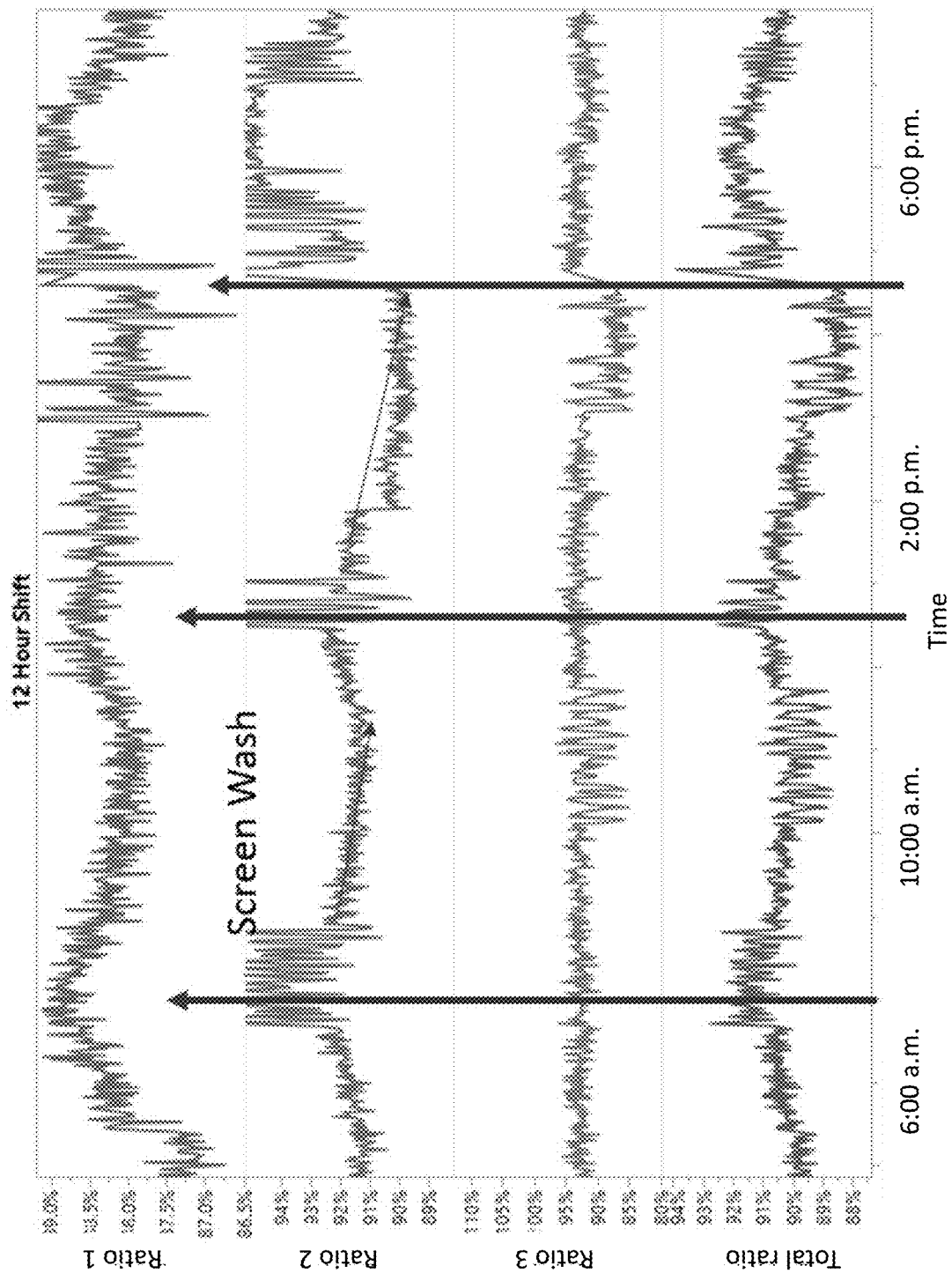
FIG. 11 is a graph showing flow rates over time through primary, secondary, and tertiary screens of a fiber separation unit in the absence of pulse dose administration of a cleaning formulation.

FIG. 11 is a graph showing how flow rate typically varies over a 12-hour timeframe in the absence of pulse dose administration of PhibroDC™ cleaning formulation through the primary screen (ratio 1), secondary screen (ratio 2), tertiary screen (ratio 3), and overall (total ratio). The data shows significant decreases in flow rates between standard screen cleanings (indicated by vertical arrows).

Figure 12:
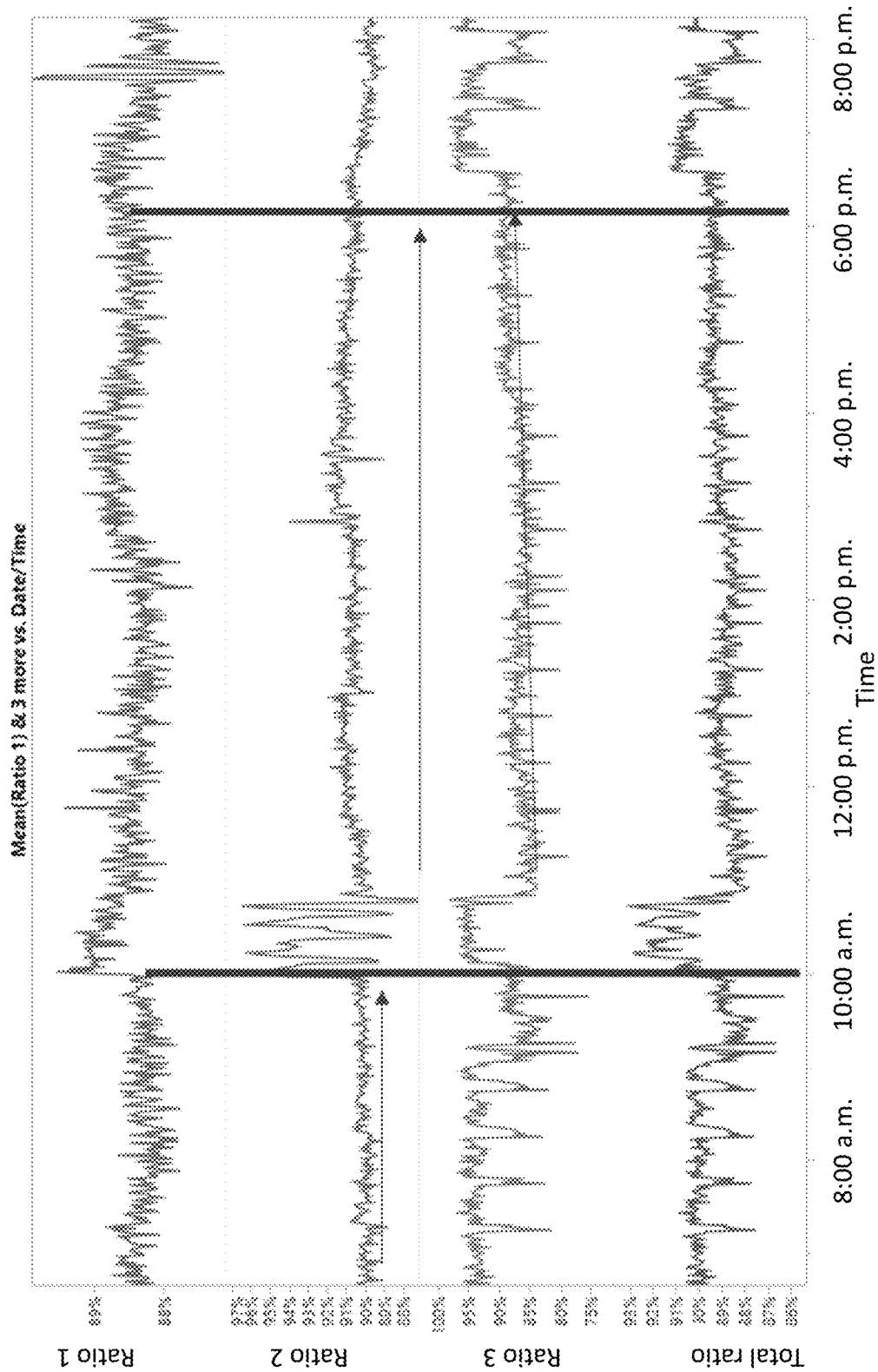
FIG. 12 is a graph showing flow rates over time through primary, secondary, and tertiary screens of a fiber separation unit with pulse dose administration of a cleaning formulation.

FIG. 12 is a comparable graph showing the effects of administering pulsed doses of PhibroDC™ cleaning formulation on flow rate over time through the primary screen (ratio 1), secondary screen (ratio 2), tertiary screen (ratio 3), and overall (total ratio). The data in FIG. 11 shows much less variability in flow rates and an increased interval between standard screen cleanings. Pulse dose administration improved the flow rate consistency, largely eliminated low flow rate occurrences, and maintained stable flow ratios without flow rate decline between screen washes.

Example 2

Figure 13A:
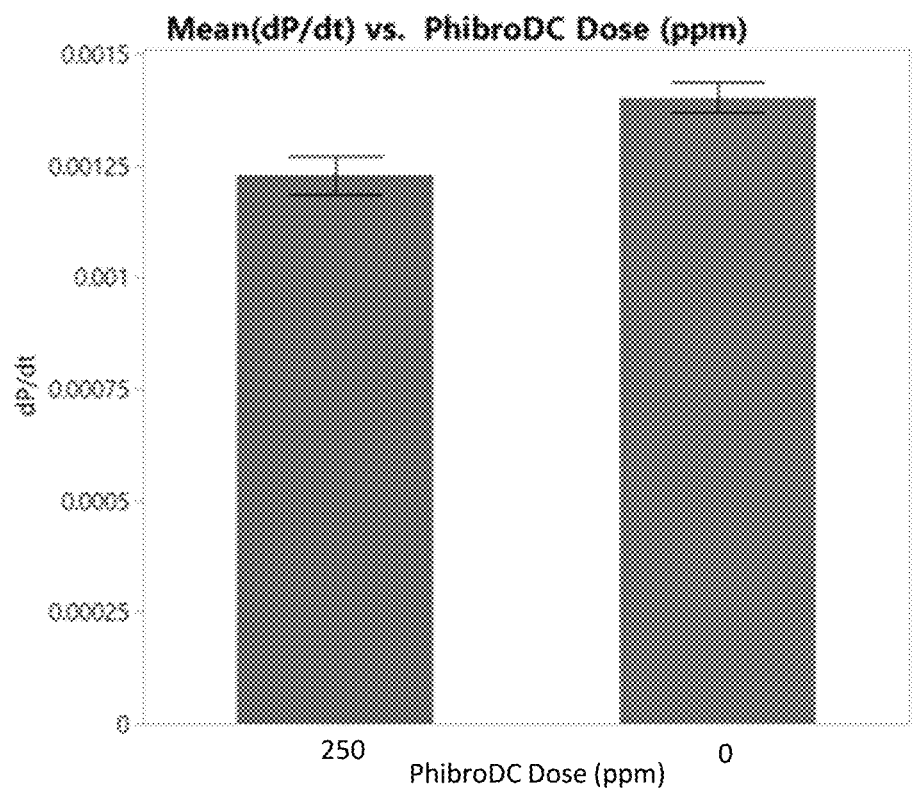
FIGS. 13A and 13B are graphs showing change in pressure over time (dP/dt) in a mash bank in the presence or absence of pulse dose administration of a cleaning formulation.
Figure 13B:
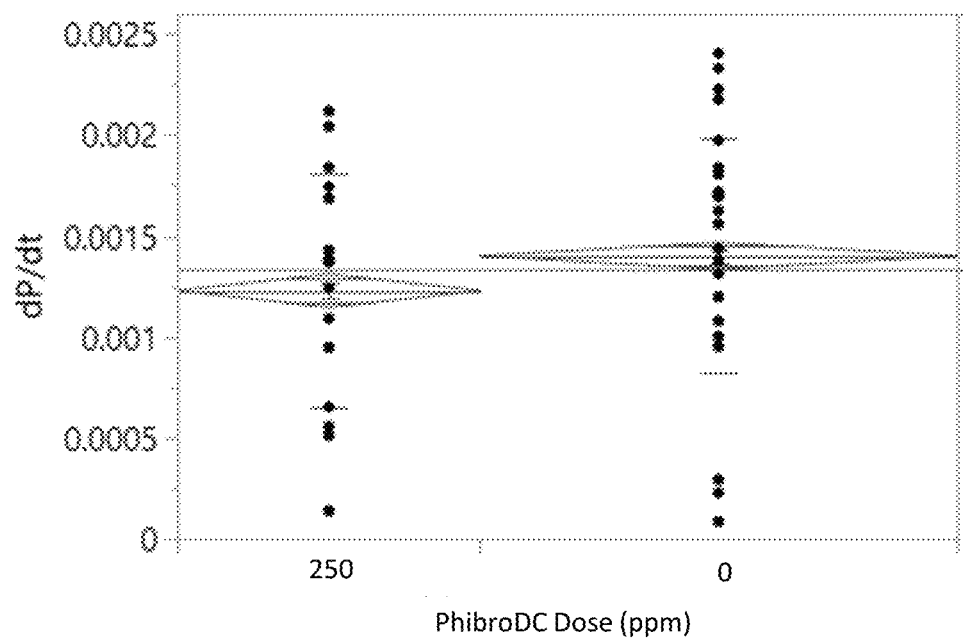

PhibroDC™ cleaning formulation was administered into a fluid process stream (corn mash) of an ethanol-processing plant using pulse dosing. The PhibroDC™ cleaning formulation was administered into the mash bank for 30 seconds every 30 minutes to provide a concentration of 250 ppm in the fluid process stream. The pressures were evaluated and normalized by the flow rate. The linear regression of the pressure/flows vs. hours the mash train was online was calculated for each cleaning cycle. The results are shown in FIGS. 13A and 13B. Advantageously, a smaller pressure increase over time resulted when the pulse dosing regimen was used.

Figure 14A:
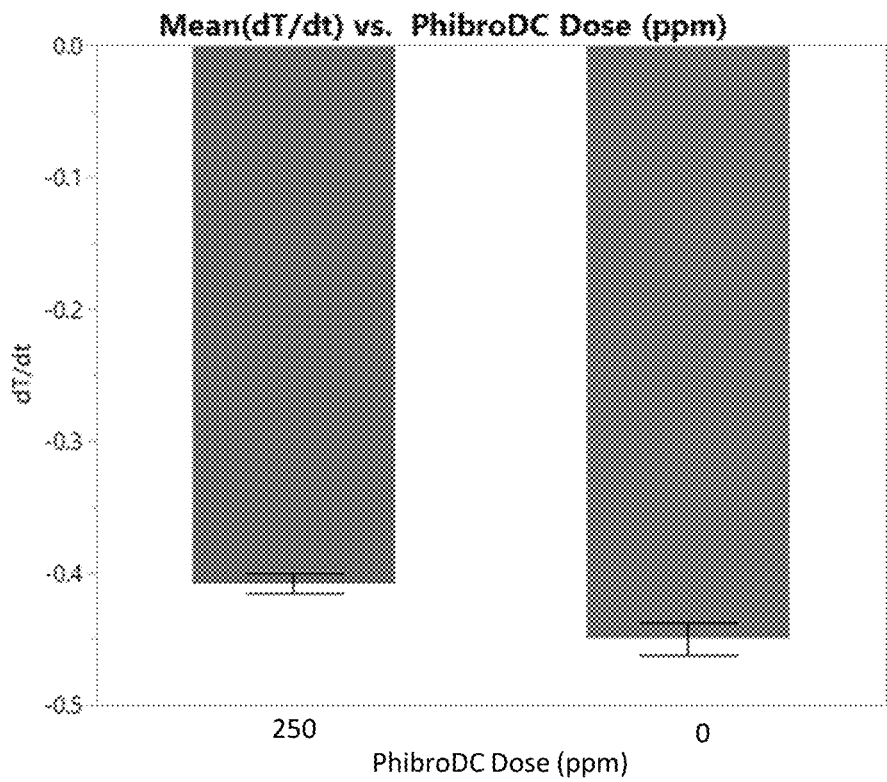
FIGS. 14A and 14B are graphs showing change in temperature over time (dT/dt) in a mash bank in the presence or absence of pulse dose administration of a cleaning formulation.
Figure 14B:
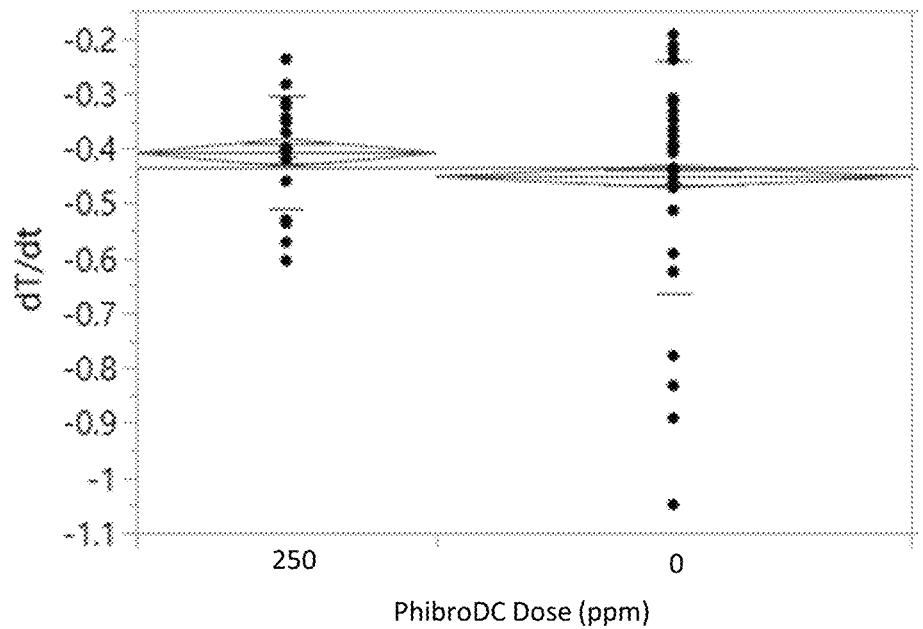

The temperature drop over time also was determined, and the linear regression of the beer-feed temperature over time was calculated for each cleaning cycle. The results are shown in FIGS. 14A and 14B. Advantageously, a smaller temperature drop over time resulted when the pulse dosing regimen was used.

Figure 15A:
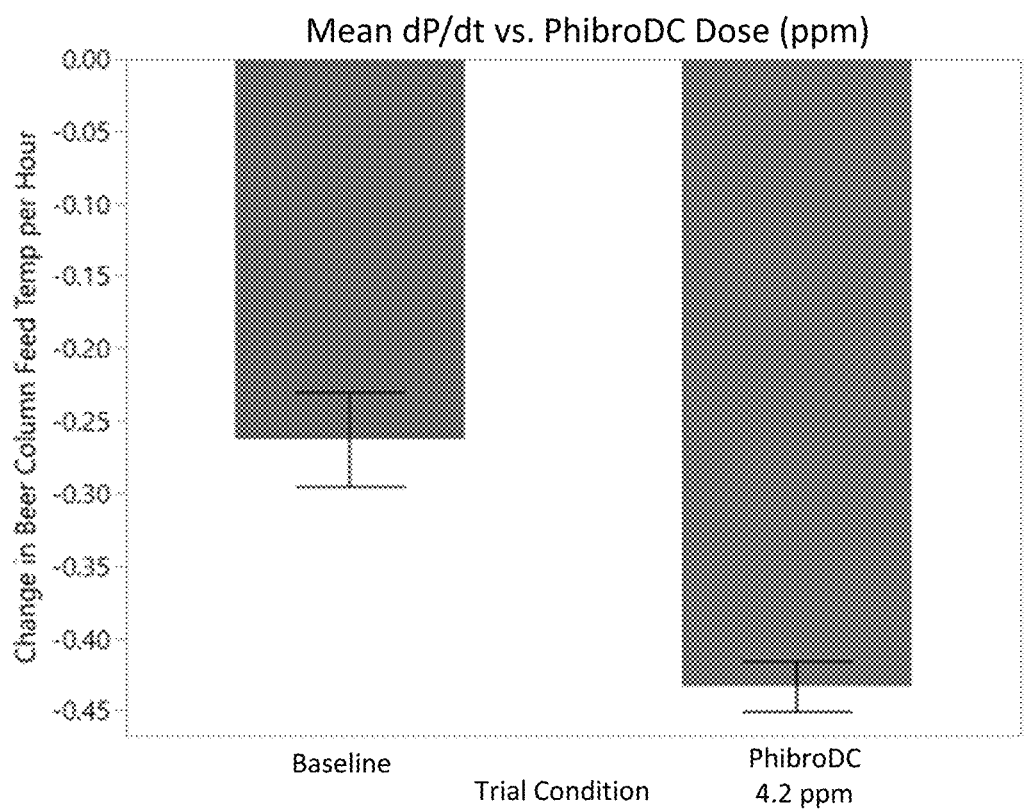
FIGS. 15A and 15B are graphs showing change in pressure over time (dP/dt) in a mash bank in the presence or absence of continuous low-dose administration of the cleaning formulation of FIGS. 13A-13B.
Figure 15B:
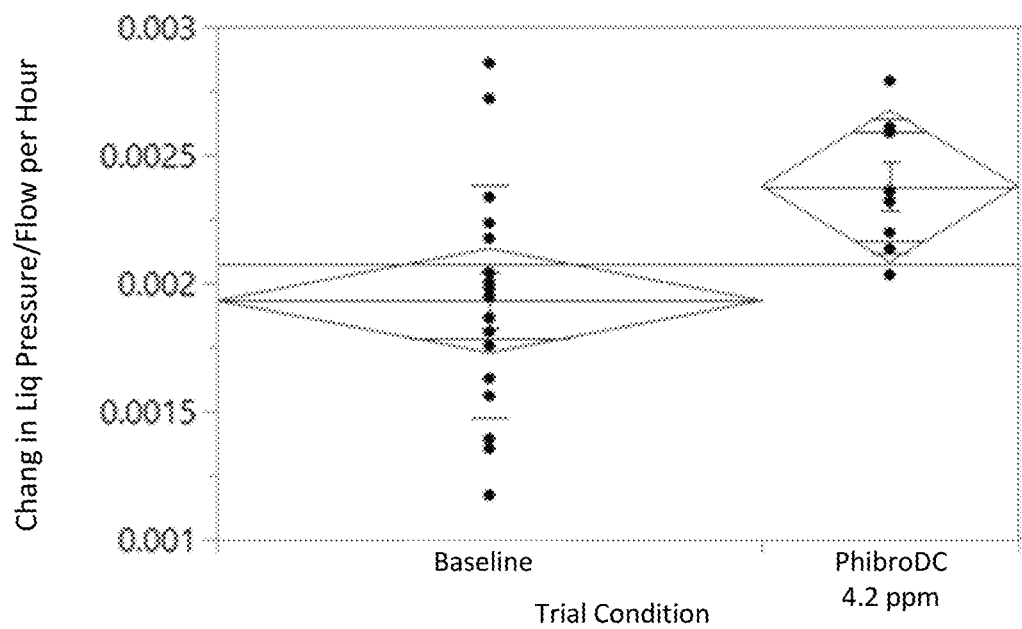

For comparison, the PhibroDC™ cleaning formulation was administered continuously into the mash bank to provide a concentration of 4.2 ppm in the fluid process stream. The 4.2 ppm continuous dose is an amount of the PhibroDC™ cleaning formulation that is equivalent to pulse dosing for 60 seconds every 60 minutes (or 30 seconds every 30 minutes) to provide a concentration of 250 ppm. The pressures were evaluated and normalized by the flow rate. The linear regression of the pressure/flows vs. hours the mash train was online was calculated for each cleaning cycle. The pressure effects are shown in FIGS. 15A and 15B. Surprisingly, continuous dosing at an equivalent lower dose had a slight negative impact (higher dP/dt) compared to the baseline (no dose). The results are in stark contrast to the pulse dosing regimen results.

Figure 16A:
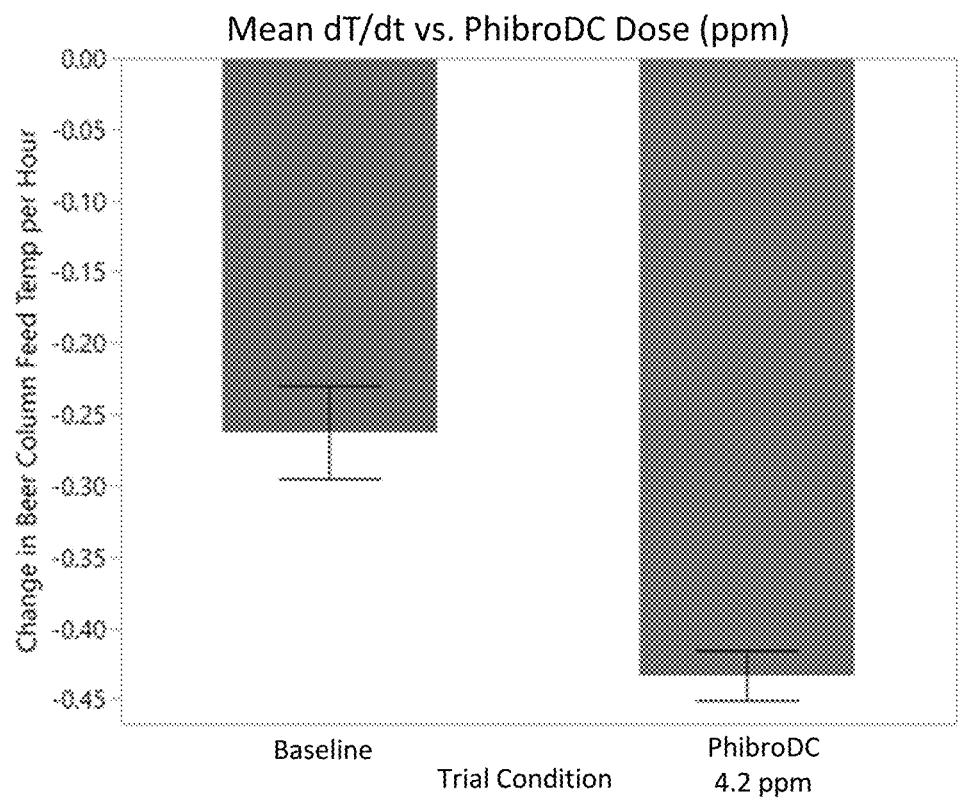
FIGS. 16A and 16B are graphs showing change in temperature over time (dT/dt) in a mash bank in the presence or absence of continuous low-dose administration of a cleaning formulation of FIGS. 14A-14B.
Figure 16B:
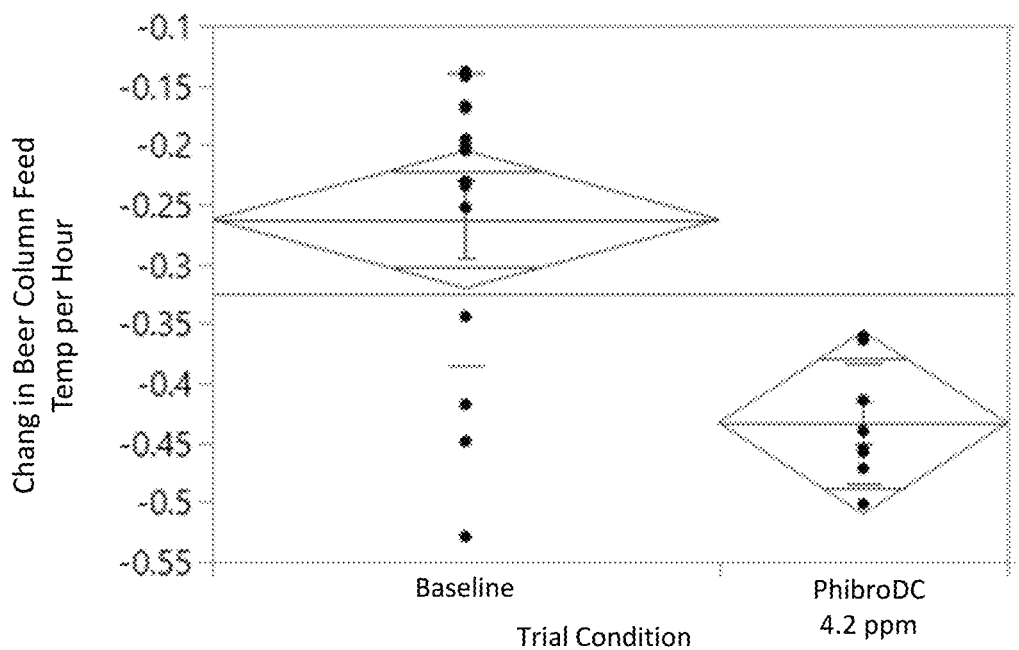

The temperature drop over time also was determined, and the linear regression of the beer-feed temperature over time was calculated. The results are shown in FIGS. 16A and 16B. Surprisingly again, continuous dosing had a negative impact (a larger dT/dt) compared to the baseline (no dose). In contrast, the pulse dosing regimen provided a clear advantage over no dose.

Figure 17A:
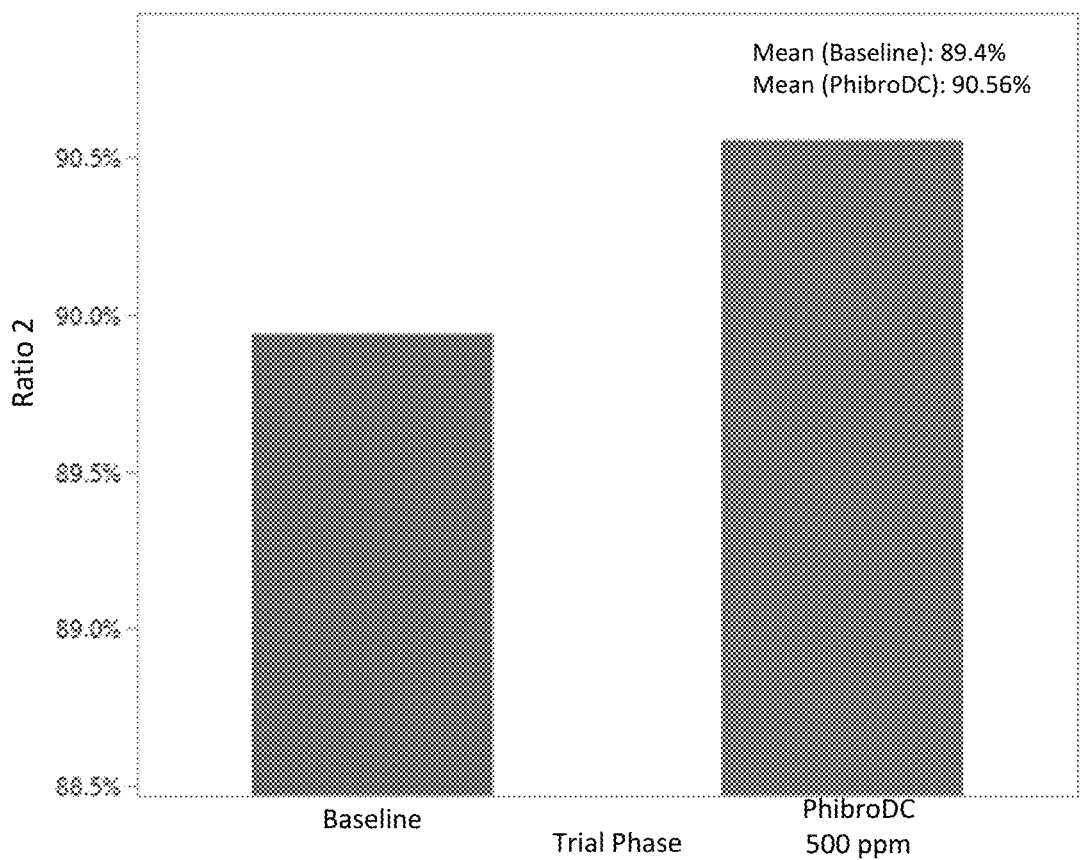
FIGS. 17A-17O are graphs showing effects of pulse dose administration of a cleaning formulation at doses of 0, 500, and 2000 ppm at a secondary screen of a fiber separation unit on flow rate through the secondary screen.
Figure 17B:
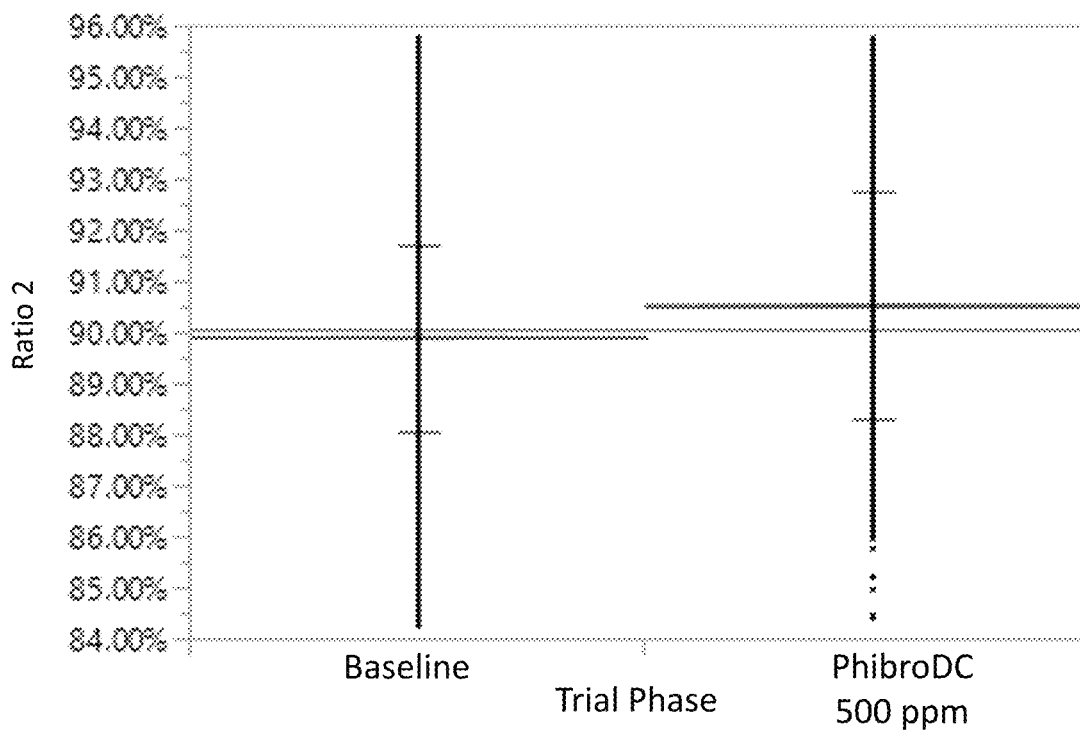
Figure 17C:
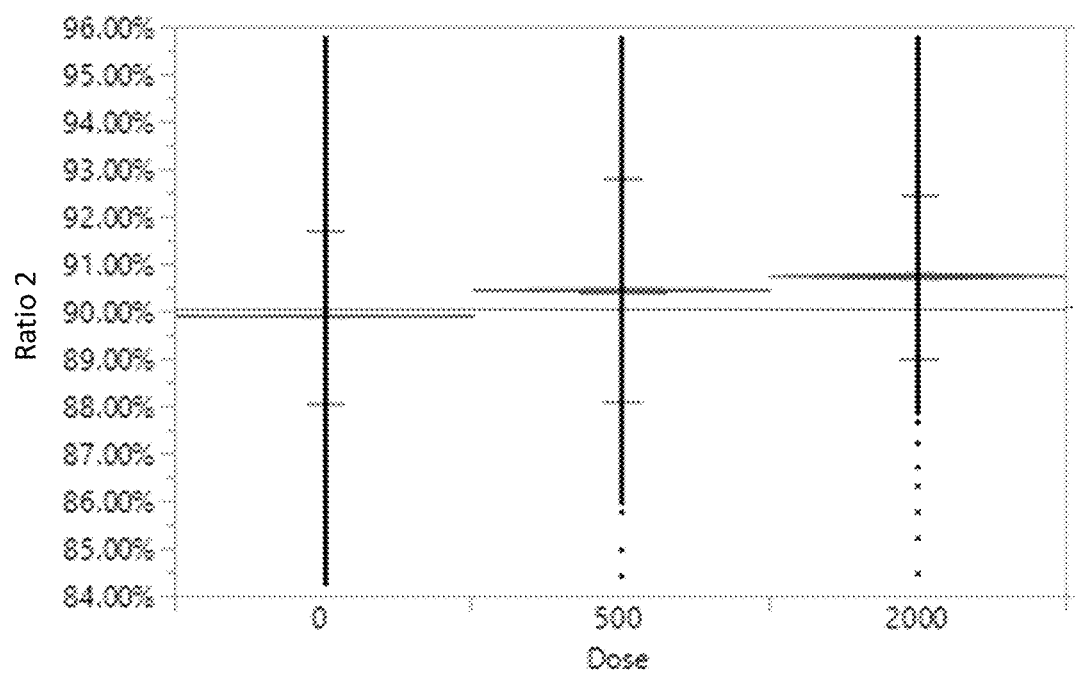

The PhibroDC™ cleaning formulation was administered to the secondary and/or tertiary screens of the fiber separation unit for 30 seconds every 30 minutes to provide 500 ppm or 2000 ppm at the secondary screen. The results of administration to the secondary screen are shown in FIGS. 17A-17O. Results were analyzed using a one-way Anova test, student's t-test, and Tukey-Kramer test. Addition of 500 ppm increased the mean ratio from 89.94% to 90.56% (FIGS. 17A, 17B). Increasing the dosage to 2000 ppm further increased the mean ratio as shown in FIG. 17C.

Figure 18A:
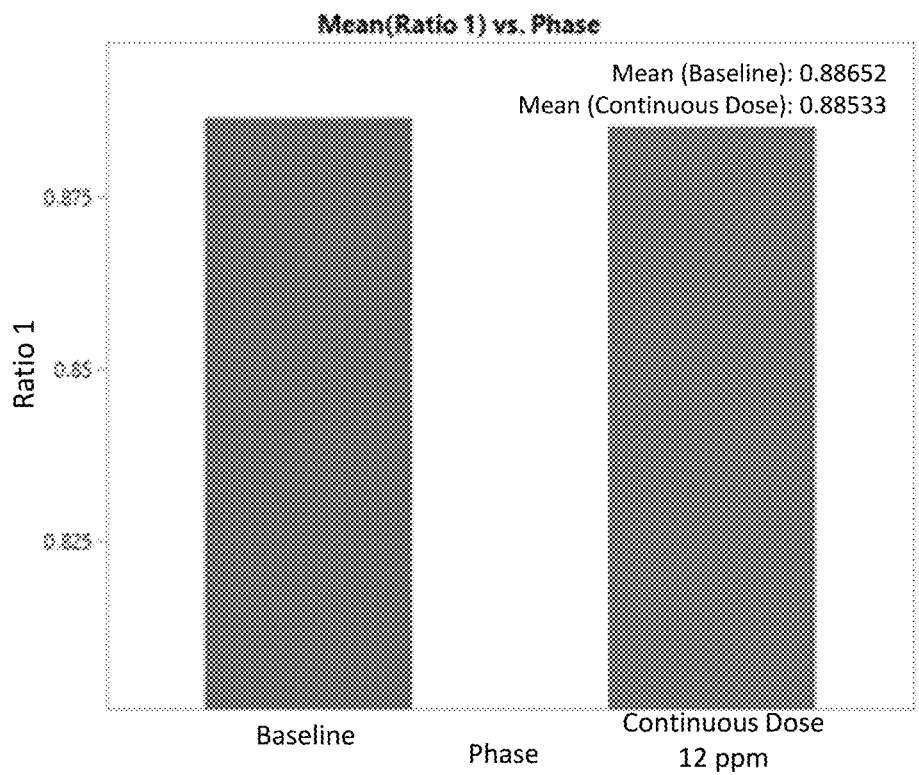
FIGS. 18A-18B are graphs showing effects of continuous low-dose administration of the cleaning formulation to a primary screen of a fiber separation unit on flow rate through the primary screen.
Figure 18B:
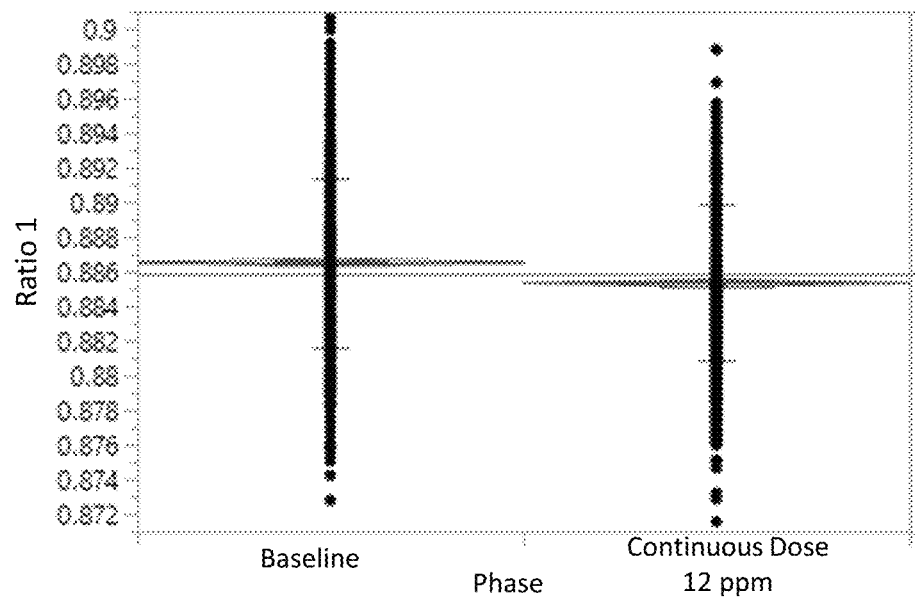
Figure 19A:
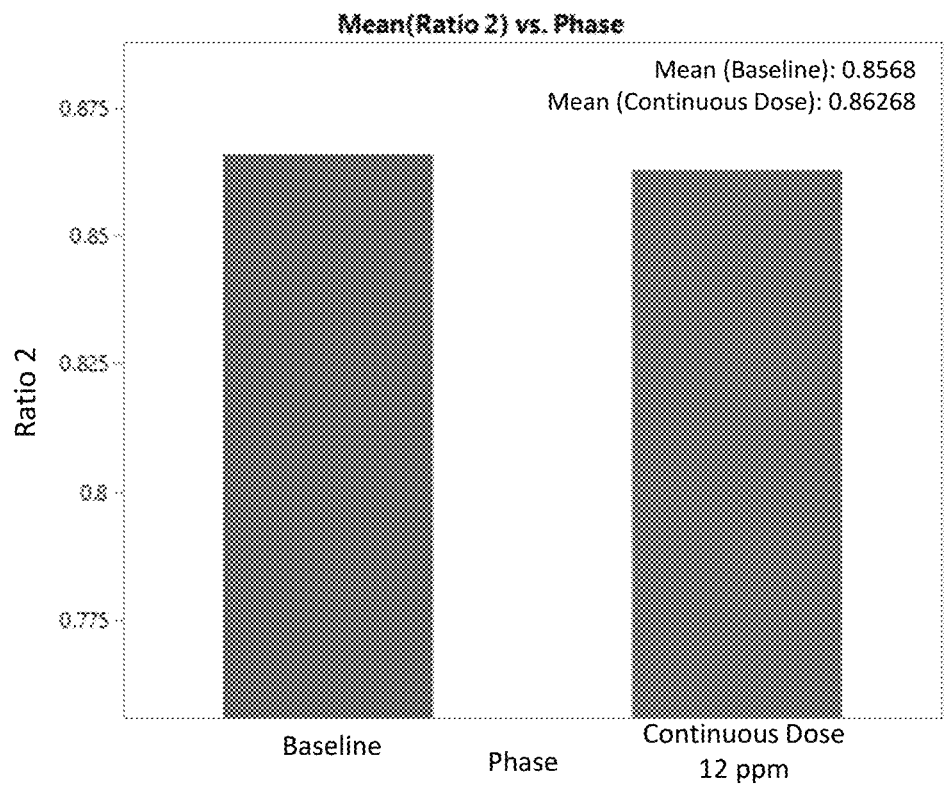
FIGS. 19A-19B are graphs showing effects of continuous low-dose administration of the cleaning formulation to a secondary screen of a fiber separation unit on flow rate through the secondary screen.
Figure 19B:
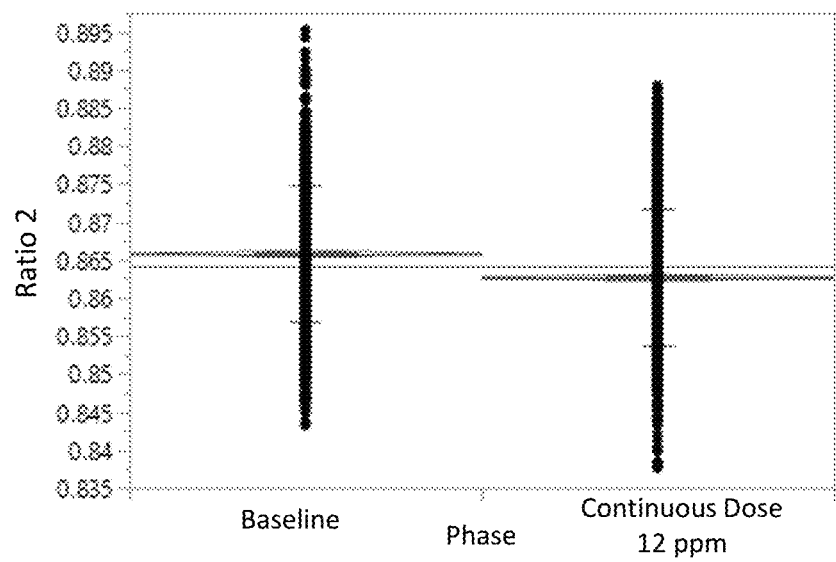
Figure 20A:
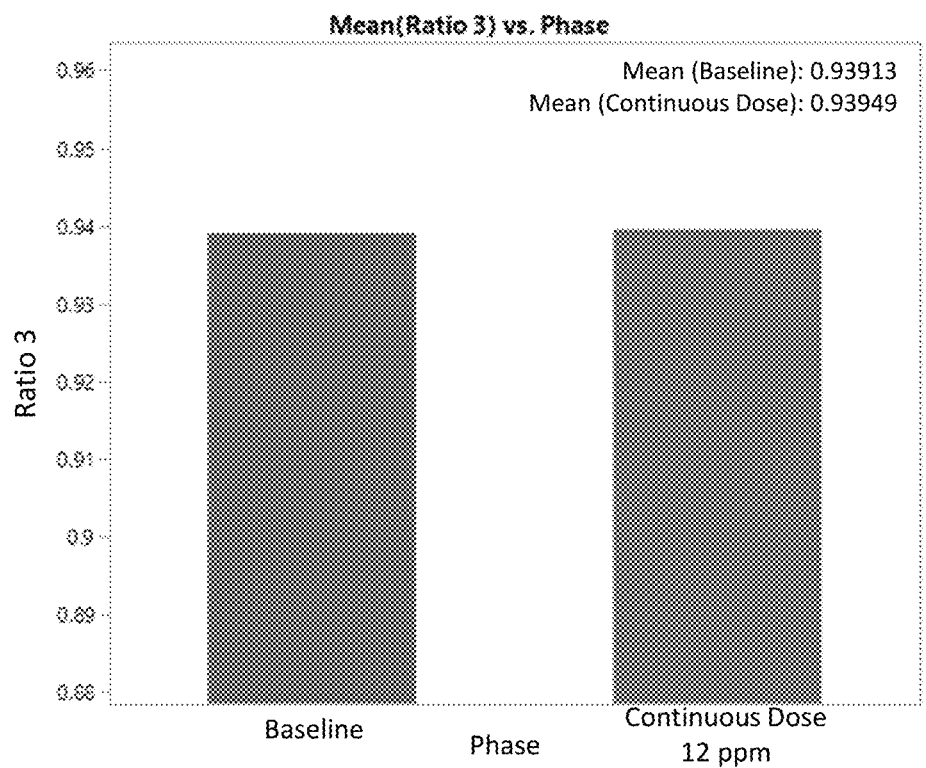
FIGS. 20A-20B are graphs showing effects of continuous low-dose administration of the cleaning formulation to a tertiary screen of a fiber separation unit on flow rate through the tertiary screen.
Figure 20B:
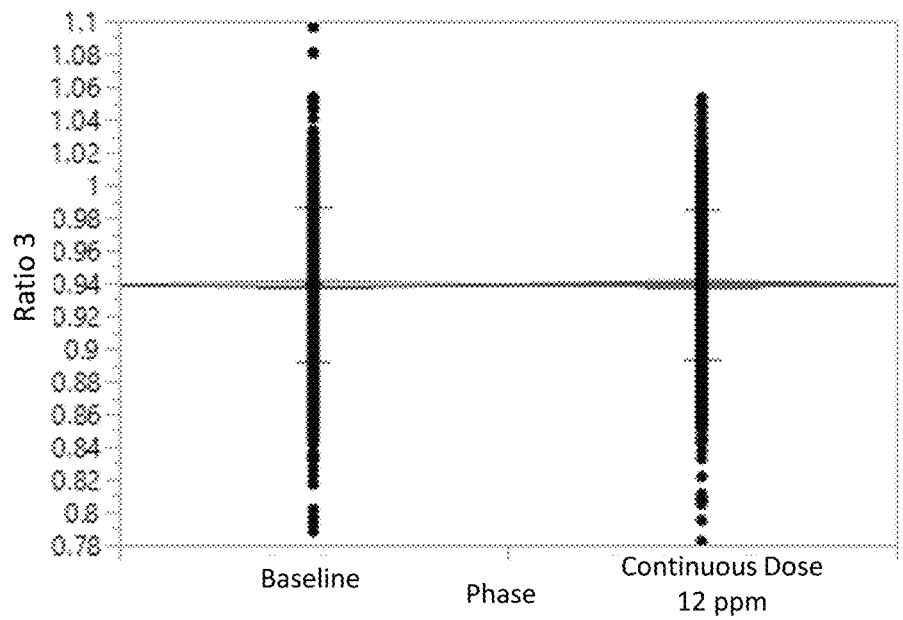

For comparison, the PhibroDC™ cleaning formulation was administered continuously to the primary, secondary, and tertiary screens of the fiber separation unit to provide a concentration of 12 ppm in the fluid process stream. The 12 ppm continuous dose is an amount of the PhibroDC™ cleaning formulation that is equivalent to pulse dosing for 60 seconds every 60 minutes (or 30 seconds every 30 minutes) to provide a concentration of 750 ppm. The results are shown in FIGS. 18A-18B (primary screen), 19A-19B (secondary screen), and 20A-20B (tertiary screen). Once again, the continuous dosing surprisingly had a slight negative impact on flow through the separation screens compared to the baseline (no dose). However, the pulse dosing regimen had a clear positive impact (see e.g., FIG. 17A—pulse dosing vs. FIG. 19A—continuous low dosing).

Example 3

A cleaning formulation is administered into a fluid process stream of a processing plant. The processing plant may be an ethanol processing plant, a protein processing plant, a corn oil processing plant, an ethanol and protein processing plant, an ethanol and corn oil processing plant, or an ethanol, corn oil and protein processing plant, and the fluid process stream may be a corn mash stream. The cleaning formulation may be pulse dosed into the fluid stream at one or more points of the processing plant, e.g., at a mash bank, a heat exchanger, an evaporator, or one or more separation screens of a separation unit. For comparison, an equivalent dose of the cleaning formulation is administered continuously at the one or more points. For example, pulse dosing to provide a concentration of 250 ppm, 500 ppm, 750 ppm, or 1000 ppm is performed for 60 seconds every 60 minutes, or 30 seconds every 30 minutes, and is compared to continuous dosing providing a concentration of 4.2 ppm, 8.3 ppm, 12.5 ppm, or 16.7 ppm, respectively. Evaluated parameters may include pressure, temperature, and/or flow rate over time. It is expected that pulse dosing to a given concentration may provide superior results as evidenced by smaller pressure increases, smaller temperature drops, smaller flow rate drops, and/or greater flow rates over time compared to continuous dosing at an equivalent lower concentration of the cleaning formulation.

Example 4

Organic matter is baked onto one or more components to mimic deposits that occur on processing plant components as the processing plant is operated. For example, organic matter may be baked onto a separation screen or an oil separator disc, or onto laboratory-sized components of similar composition to components used in the processing plant. The components with baked-on organic matter are immersed continuously or intermittently in a fluid (e.g., a corn mash) containing a cleaning solution. The components are immersed in fluids containing 250 ppm, 500 ppm, 750 ppm, or 1000 ppm of the cleaning formulation for 30 seconds every 30 minutes, or 60 seconds every 60 minutes, for a period of time. The period of time may be 2 hours, 4 hours, 6 hours, 8 hours, 12 hours, 18 hours, or 24 hours. Components prepared the same way are continuously immersed in fluids containing an equivalent dose, i.e., 4.2 ppm, 8.3 ppm, 12.5 ppm, or 16.7 ppm cleaning formulation, respectively, for the same period of time. Components also may be immersed in fluids containing no cleaning formulation for the same period of time. The fluids may be maintained at a temperature similar to temperatures employed at the processing plant. When the period of time has elapsed, the components are evaluated. The amount of organic matter remaining on the components is evaluated (e.g., visually) and the ease of removing the organic matter is evaluated. Different cleaning methods, such as pressure washing, hydroblasting, cleaning with caustics, and/or other suitable methods, are evaluated to compare the effects of pulse dosing, continuous dosing, and, optionally, no dosing. It is expected that pulse dosing may provide superior results as evidenced by easier cleaning of components subjected to pulse dosing to a given concentration compared to components subjects to continuous immersion in fluids with an equivalent lower concentration of the cleaning formulation or in fluids with no cleaning formulation.

In view of the many possible embodiments to which the principles of the present disclosure may be applied, it should be recognized that the illustrated embodiments are only preferred examples of the present disclosure and should not be taken as limiting. Rather, the scope of the present disclosure is defined by the following claims. I therefore claim as my invention all that comes within the scope and spirit of these claims.

I claim:

1. A method, comprising cleaning a structural component of a processing facility by using pulse dosing to administer a cleaning formulation into a fluid process stream flowing through structural components of the processing facility, the fluid process stream comprising (i) corn, or (ii) a rinse fluid, a cleaning fluid, or any combination thereof,
wherein pulse dosing comprises administering the cleaning formulation into the fluid process stream for a period of x seconds every y minutes, with no administration of the cleaning formulation between the periods of x seconds, wherein x and y independently are from 15 to 90.

2. The method of claim 1, wherein x=y.

3. The method of claim 1, wherein an amount of the cleaning formulation is administered into the fluid process stream to provide a concentration of 10 ppm to 50,000 ppm of the cleaning formulation in the fluid process stream during the period of x seconds.

4. The method of claim 1, wherein the processing facility is an ethanol processing plant, a protein processing plant, a corn oil processing plant, an ethanol and corn oil processing plant, an ethanol and protein processing plant, or an ethanol, corn oil and protein processing plant.

5. The method of claim 1, wherein the cleaning formulation comprises a detergent, a scale inhibitor, a pH modifier, an oxidizer, a caustic solution, or any combination thereof.

6. The method of claim 4, wherein the processing facility comprises one or more structural components selected from a heating and liquefaction unit, a heat exchanger unit, a propagation unit, a fermentation unit, a distillation unit, an evaporation unit, a centrifuge unit, a fiber separation unit, a protein separation unit, an oil separation unit, or any combination thereof.

7. The method of claim 6, wherein the cleaning formulation is administered into the fluid process stream at, or upstream of, at least one of the one or more structural components.

8. The method of claim 6, wherein pulse dosing is performed at each of at least two of the one or more of the structural components of the processing facility for a period of x seconds every y minutes, with no administration of the cleaning formulation between the periods of x seconds at each of the at least two of the one or more structural components, wherein each x and y independently is from 15 to 90.

9. The method of claim 6, wherein the fluid process stream comprises corn, and wherein:
   (i) the cleaning formulation is administered into, or upstream of, the heating and liquefaction unit, and a mean pressure increase over time within the heating and liquefaction unit is smaller than a mean pressure increase over time when the cleaning formulation is not administered using pulse dosing; or
   (ii) the cleaning formulation is administered into, or upstream of, the heat exchange unit, and a mean pressure increase over time within the heat exchange unit is smaller than a mean pressure increase over time when the cleaning formulation is not administered using pulse dosing; or
   (iii) the cleaning formulation is administered into, or upstream of, the heating and liquefaction unit, and a mean temperature drop over time within the heating and liquefaction unit is smaller than a mean temperature drop over time when the cleaning formulation is not administered using pulse dosing; or
(iv) the cleaning formulation is administered into, or upstream of, the heat exchanger unit, and a mean temperature drop over time within the heat exchanger unit is smaller than a mean temperature drop over time when the cleaning formulation is not administered using pulse dosing; or
(v) the cleaning formulation is administered into, or upstream of, the fiber separation unit, and a mean flow rate over a period of time through the fiber separation unit is greater than a mean flow rate over the period of time through the fiber separation unit when the cleaning formulation is not administered using pulse dosing; or
(vi) the cleaning formulation is administered into, or upstream of, the protein separation unit, and a mean flow rate over a period of time through the protein separation unit is greater than a mean flow rate over the period of time through the protein separation unit when the cleaning formulation is not administered using pulse dosing; or
(vii) the cleaning formulation is administered into, or upstream of, the oil separation unit, and a mean flow rate over a period of time through the oil separation unit is greater than a mean flow rate over the period of time through the oil separation unit when the cleaning formulation is not administered using pulse dosing; or
(viii) any combination of (i)-(vii).

10. The method of claim 6, wherein the fluid process stream comprises the rinse fluid, the cleaning fluid, or a combination thereof, the method further comprising:
ceasing flow of a product process stream comprising corn through at least one of the one or more structural components;
initiating flow of the fluid process stream comprising the rinse fluid, the cleaning fluid, or the combination thereof through the at least one of the one or more structural components; and
using pulse dosing to administer the cleaning formulation into the fluid process stream comprising the rinse fluid, the cleaning fluid, or the combination thereof.

11. The method of claim 7, wherein the cleaning formulation is administered into the fluid process stream in, or upstream of, the heating and liquefaction unit, the heat exchanger unit, the evaporation unit, the fiber separation unit, the protein separation unit, the oil separation unit, or any combination thereof.

12. The method of claim 8, wherein an amount of the cleaning formulation administered into the fluid process stream at each of the at least two of the one or more structural components independently provides a concentration of 10 ppm to 50,000 ppm of the cleaning formulation in the fluid process stream.

13. The method of claim 8, wherein:
(i) x=y at each one of the two or more structural components; or
(ii) x and y at a first structural component of the at least two of the one or more structural components are different than x and y, respectively, at a second structural component of the at least two of the one or more structural components; or
(iii) an amount of the cleaning formulation administered at a first structural component of the at least two of the one or more structural components provides a different concentration of the cleaning formulation in the fluid process stream than an amount of the cleaning formulation administered at a subsequent structural component of the at least two of the one or more structural components; or
(iv) a chemical composition of the cleaning formulation administered at a first structural component of the at least two of the one or more structural components is different than a chemical composition of the cleaning formulation administered at a subsequent structural component of the at least two of the one or more structural components; or
(v) any combination of (i), (ii), (iii), and (iv).

14. The method of claim 10, wherein:
(i) pulse dosing comprises administering the cleaning formulation into the fluid process stream comprising the rinse fluid, the cleaning fluid, or the combination thereof for a period of x seconds every y minutes, with no administration of the cleaning formulation between the periods of x seconds, wherein x and y independently are from 15 to 90; or
(ii) an amount of the cleaning formulation is administered into the fluid process stream comprising the rinse fluid, the cleaning fluid, or the combination thereof to provide a concentration of 10 ppm to 50,000 ppm of the cleaning formulation in the fluid process stream during the period of x seconds; or
(iii) both (i) and (ii).

15. A method, comprising cleaning a structural component of a processing facility by using pulse dosing to administer a cleaning formulation into a fluid process stream flowing through structural components of the processing facility, the fluid process stream comprising (i) corn, or (ii) a rinse fluid, a cleaning fluid, or any combination thereof,
wherein the processing facility is an ethanol processing plant, a protein processing plant, a corn oil processing plant, an ethanol and corn oil processing plant, an ethanol and protein processing plant, or an ethanol, corn oil and protein processing plant,
wherein the processing facility comprises one or more structural components selected from a heating and liquefaction unit, a heat exchanger unit, a propagation unit, a fermentation unit, a distillation unit, an evaporation unit, a centrifuge unit, a fiber separation unit, a protein separation unit, an oil separation unit, or any combination thereof, and
wherein the fiber separation unit comprises one or more separation screens and the cleaning formulation is administered upstream of at least one of the one or more of the separation screens.

16. The method of claim 15, wherein:
the fiber separation unit comprises a primary separation screen, a secondary separation screen, and a tertiary separation screen;
the cleaning formulation is administered via pulse dosing to the secondary separation screen to provide a first concentration of the cleaning formulation in the fluid process stream at or proximate the secondary separation screen; and
the cleaning formulation is administered via pulse dosing to the tertiary separation screen to provide a second concentration of the cleaning formulation in the fluid process stream at or proximate the tertiary separation screen.

17. The method of claim 16, wherein the second concentration is less than the first concentration.

18. A method of cleaning structural components of a processing facility, the method comprising cleaning the structural components of the processing facility by using pulse dosing to administer a cleaning formulation into a fluid process stream flowing through structural components of the processing facility using pulse dosing, wherein:
- the processing facility is an ethanol processing plant, a protein processing plant, a corn oil processing plant, an ethanol and protein processing plant, an ethanol and corn oil processing plant, or an ethanol, corn oil and protein processing plant;
- the fluid process stream comprises (i) corn, or (ii) a rinse fluid;
- pulse dosing comprises administering the cleaning formulation into the fluid process stream for a period of x seconds every y minutes, with no administration of the cleaning formulation between the periods of x seconds;
- x and y independently are from 1 to 150;
- x=y; and
- an amount of the cleaning formulation is administered into the fluid process stream to provide a concentration of 10 ppm to 50,000 ppm of the cleaning formulation in the fluid process stream during the period of x seconds.

* * * * *